US011285202B2

(12) United States Patent
Wang et al.

(10) Patent No.: US 11,285,202 B2
(45) Date of Patent: Mar. 29, 2022

(54) POLYMER-PROTEIN CORE-SHELL PARTICLES AS EFFECTIVE VACCINE DELIVERY VEHICLES AND TREATMENTS METHODS USING THE SAME

(71) Applicant: University of South Carolina, Columbia, SC (US)

(72) Inventors: Qian Wang, Columbia, SC (US); L. Andrew Lee, Columbia, SC (US)

(73) Assignee: University of South Carolina, Columbia, SC (US)

( * ) Notice: Subject to any disclaimer, the term of this patent is extended or adjusted under 35 U.S.C. 154(b) by 74 days.

(21) Appl. No.: 15/416,429

(22) Filed: Jan. 26, 2017

(65) Prior Publication Data

US 2017/0209559 A1 Jul. 27, 2017

Related U.S. Application Data

(60) Provisional application No. 62/287,035, filed on Jan. 26, 2016.

(51) Int. Cl.
*A61K 39/12* (2006.01)
*A61K 39/015* (2006.01)
*A61K 39/00* (2006.01)

(52) U.S. Cl.
CPC ............ *A61K 39/12* (2013.01); *A61K 39/015* (2013.01); *A61K 2039/575* (2013.01); *A61K 2039/6031* (2013.01); *A61K 2039/6093* (2013.01); *A61K 2039/64* (2013.01); *C07K 2319/24* (2013.01); *C12N 2770/24122* (2013.01); *C12N 2770/24134* (2013.01)

(58) Field of Classification Search
CPC ...... A61K 39/015; A61K 39/02; A61K 39/12; A61K 2039/57; A61K 2039/575; A61K 2039/6031; A61K 2039/6093; A61K 2039/64; C07K 2319/24; C12N 2770/24122; C12N 2770/24134
See application file for complete search history.

(56) References Cited

U.S. PATENT DOCUMENTS

2007/0009552 A1* 1/2007 Whitehead ............ A61K 39/12 424/218.1
2010/0112072 A1* 5/2010 Wang .................. A61K 9/5138 424/490
2011/0268804 A1* 11/2011 Shi ........................ A61P 31/00 424/489

OTHER PUBLICATIONS

Stano, Protein antigen using polymersomes, Biomaterials p. 4339 (Year: 2013).*
Liu High epitope density, Vaccine p. 366 (Year: 2004).*
World Health Organization, http://www.who.int/mediacentre/factsbeets/fs117/en/.
Jia, F.; Liu, X.; Li, L.; Mallapragada, S.; Narasimhan, B.; Wang, Q. "Multifunctional nanoparticles for targeted delivery of immune activating and cancer therapeutic agents" J. Control. Release 2013, 172, 1020-1034.
Mandal, B.; Bhattacharjee, H.; Mittal, N.; Sah, H.; Balabathula, P.; Thoma, L. A.; Wood, G. C. "Core-shell-type lipid-polymer hybrid nanoparticles as a drug delivery platform" Nanomedicine 2013, 9, 474-491.
Kumar, S.; Tummala, H. "Development of Soluble Inulin Microparticles as a Potent and Safe Vaccine Adjuvant and Delivery System" Mol. Pharmaceutics 2013, 10, 1845-1853.
Yao, W.; Peng, Y.; Du, M.; Luo, J.; Zong, L. "Preventative Vaccine-Loaded Mannosylated Chitosan Nanoparticles Intended for Nasal Mucosal Delivery Enhance Immune Responses and Potent Tumor Immunity" Mol. Pharmaceutics 2013, 10, 2904-2914.
Abstract of Cooper, D. L.; Conder, C. M.; Harirforoosh, S. Expert Opin. Drug Deliv. 2014, 11, 1661-1680.
Cleland, J. L. "Single-administration vaccines: controlled release technology to mimic repeated immunizations" Trends Biotechnol. 1999, 17, 25-29.
Puffer, E. B.; Pontrello, J.K.; Hollenbeck, J. J.; Kink, J. A.; Kiessling, L. L. "Activating B Cell Signaling with Defined Multivalent Ligands" ACS Chem. Biol. 2007, 2, 252-262.
Demento, S. L.; Cui, W.; Criscione, J. M.; Stern, E.; Tulipan, J.; Kaech, S. M.; Fahmy, T. M. "Role of sustained antigen release from nanoparticle vaccines in shaping the T cell memory phenotype" Biomaterials 2012, 33, 4957-4964.
Russell, J. T.; Lin, Y.; Böker, A.; Su, L.; Carl, P.; Zettl, H.; He, J.; Sill, K.; Tangirala, R.; Emrick, T.; Littrell, K.; Thiyagarajan, P.; Cookson, D.; Fery, A.; Wang, Q.; Russell, T. P. "Self-Assembly and Cross-Linking of Bionanoparticles at Liquid-Liquid Interfaces" Angew. Chem., Int. Ed. 2005, 44, 2420-2426.
Li, T.; Niu, Z.; Emrick, T.; Russell, T. R.; Wang, Q. "Core/Shell Biocomposites from the Hierarchical Assembly of Bionanoparticles and Polymer" Small 2008, 4, 1624-1629.
Li, T.; Wu, L.; Suthiwangcharoen, N.; Bruckman, M. A.; Cash, D.; Hudson, J. S.; Ghoshroy, S.; Wang, Q. "Controlled assembly of rodlike viruses with polymers" Chem. Commun. (Camb) 2009, 28, 2869-2871.
Li, T.; Ye, B.; Niu, Z.; Thompson, P.; Seifert, S.; Lee, B.; Wang, Q. "Closed-Packed Colloidal Assemblies from Icosahedral Plant Virus and Polymer" Chem. Mater. 2009, 21, 1046-1050.
Suthiwangcharoen, N.; Li, T.; Li, K.; Thompson, P.; You, S. J.; Wang, Q. "M13 Bacteriophage-Polymer Nanoassemblies as Drug Delivery Vehicles" Nano Res. 2011, 4, 483-493.
Wu, L.; Li, T.; Blom, D.; Zhao, J.; Ghoshroy, S.; Wang, Q. "Synthesis and Electron Microscopic Analysis of the Self-Assembly of Polymer and Ferritin Core-Shell Structures" Microsc. Res. Tech. 2011, 74, 636-641.
Suthiwangcharoen, N.; Li, T.; Wu, L.; Reno, H. B.; Thompson, P.; Wang, Q. "Facile Co-Assembly Process to Generate Core-Shell Nanoparticles with Functional Protein Corona" Biomacromolecules 2014, 15, 948-956.

(Continued)

*Primary Examiner* — Matthew P Coughlin
*Assistant Examiner* — Thurman Wheeler
(74) *Attorney, Agent, or Firm* — Dority & Manning, P.A.

(57) ABSTRACT

A polymer-protein core-shell nanoparticle is generally provided. In one embodiment, the polymer-protein core-shell nanoparticle includes a pyridinyl group grafted polymer assembled with a protein or a glycoprotein based antigen to form a core-shell particle. A method is also generally provided for treating an infected organism. In one embodiment, the method includes administering the polymer-protein core-shell nanoparticle to the infected organism.

15 Claims, 26 Drawing Sheets

(56) References Cited

OTHER PUBLICATIONS

Lynch, I.; Dawson, K. A. "Protein-nanoparticle interactions." Nano Today 2008, 3, 40-47.
Mahmoudi, M.; Lynch, I.; Ejtehadi, M. R.; Monopoli, M. P.; Bombelli, F. B.; Laurent, S. "Protein Nanoparticle Interactions: Opportunities and Challenges" Chem. Rev. 2011, 111, 5610-5637.
Abstract of Lopez, J. A.; Roggero, M. A.; Duombo, O.; Gonzalez, J. M.; Tolle, R.; Koita, O.; Arevalo-Herrera, M.; Herrera, S.; Corradin, G. "Recognition of Synthetic 104-Mer and 102-Mer Peptides Corresponding to N- and C-Terminal Nonrepeat Regions of the Plasmodium Falciparum Circumsporozoite Protein by Sera from Human Donors." Am. J. Trop. Med. Hyg. 1996, 55, 424-429.
Alonso, P. L.; Sacarlal, J.; Aponte, J. J.; Leach, A.; Macete, E.; Milman, J.; Mando-Mando, I.; Spiessens, B.; Guinovart, C.; Espasa, M.; Bassat, Q.; Aide, P.; Ofori-Anyinam, O.; Navia, M. M.; Corachan, S.; Ceuppens, M.; Dubois, M. C.; Demoitie, M. A.; Dubovsky, F.; Menendez, C.; Tornieporth, N.; Ballou, W. R.; Thompson, R. Cohen J. "Efficacy of the RTS,S/AS02A vaccine against Plasmodium falciparum infection and disease in young African children: randomised controlled trial" Lancet. 2004, 364, 1411-1420.
Kumar, K.A., Sano, G., Boscardin, S., Nussenzweig, R.S., Nussenzweig, M.C., Zavala, F., and Nussenzweig, V. "The circumsporozoite protein is an immunodominant protective antigen in irradiated sporozoites" Nature 2006, 444, 937-940.
Singh, A. P.; Buscaglia, C. A.; Wang, Q.; Levay, A.; Nussenzweig D. R.; Walker, J. R.; Winzeler, E. A.; Fujii, H.; Fontoura, B. M.; Nussenzweig, V. "Plasmodium Circumsporozoite Protein Promotes the Development of the Liver Stages of the Parasite" Cell 2007, 131, 492-504.
Rico-Hesse, R. "Dengue virus evolution and virulence models." Clin. Infect. Dis. 2007, 44, 1462-1466.
Lok, S. M.; Kostyuchenko, V.; Nybakken, G. E.; Holdaway, H. A.; Battisti, A. J.; Sukupolvi-Petty, S.; Sedlak, D.; Fremont, D. H.; Chipman, P. R.; Roehrig, J. T.; Diamond, M. S.; Kuhn, R. J.; Rossmann, M. G. "Binding of a neutralizing antibody to dengue virus alters the arrangement of surface glycoproteins" Nat. Struct. Mol. Biol. 2008, 15, 312-317.
Pierson, T. C.; Diamond, M. S. "Molecular mechanisms of antibody-mediated neutralisation of flavivirus infection" Expert Rev. Mol. Med. 2008, 10, e12.
Weaver, S. C.; Reisen, W. K. "Present and future arboviral threats" Antiviral Res. 2010, 85, 328-345.
Beltramello, M.; Williams, K. L.; Simmons, C. P.; Macagno, A.; Simonelli, L.; Quyen, N. T.; Sukupolvi-Petty, S.; Navarro-Sanchez, E.; Young, P. R.; De Silva, A. M.; Rey, F. A.; Varani, L.; Whitehead, S. S.; Diamond, M. S.; Harris, E.; Lanzavecchia, A.; Sallusto, F. "The Human Immune Response to Dengue Virus Is Dominated by Highly Cross-Reactive Antibodies Endowed with Neutralizing and Enhancing Activity" Cell Host Microbe. 2010, 8, 271-283.
Tharakaraman, K.; Robinson, L. N.; Hatas, A.; Chen, Y. L.; Siyue, L.; Raguram, S.; Sasisekharan, V.; Wogan, G. N.; Sasisekharan, R. "Redesign of a cross-reactive antibody to dengue virus with broad-spectrum activity and increased in vivo potency" Proc. Nat. Acad. Sci. USA 2013, 110, E1555-1564.
Sabchareon, A.; Wallace, D.; Lang, J.; Bouckenooghe, A.; Moureau, A. "Efficacy of tetravalent dengue vaccine in Thai school children" Lancet 2013, 381, 1094-1095.
Dash, T. K.; Konkimalla, V. B. "Poly-ϵ-caprolactone based formulations for drug delivery and tissue engineering: A review" J. Control. Release 2012, 158, 15-33.
Liu, S.; Tobias, R.; McClure, S.; Styba, G.; Shi, Q.; Jackowski, G. "Removal of Endotoxin from Recombinant Protein Preparations" Clin. Biochem. 1997, 30, 455-463.
Li, T.; Niu, Z.; Suthiwangcharoen, N.; Li, R.; Prevelige, P. E.; Wang, Q. "Polymer-virus core-shell structures prepared via co-assembly and template synthesis methods" Sci. China 2010, 53, 71-77.
Reece, W. H.; Pinder, M.; Gothard, P. K.; Milligan, P.; Bojang, K.; Doherty, T.; Plebanski, M.; Akinwunmi, P.; Everaere, S.; Watkins, K. R.; Voss, G.; Tornieporth, N.; Alloueche, A.; Greenwood, B. M.; Kester, K. E.; McAdam, K. P.; Cohen, J.; Hill, A. V. A "CD4+ T-cell immune response to a conserved epitope in the circumsporozoite protein correlates with protection from natural Plasmodium falciparum infection and disease" Nat. Med. 2004, 10, 406-410.
Jalloh, A.; Jalloh, M.; Matsuoka, H. "T-cell epitope polymorphisms of the Plasmodium falciparum circumsporozoite protein among field isolates from Sierra Leone: age-dependent haplotype distribution?" Malar. J. 2009, 8, 120.
Abstract of Gamvrellis, A.; Leong, D.; Hanley, J. C.; Xiang, S. D.; Mottram, P.; Plebanski, M. "Vaccines that facilitate antigen entry into dendritic cells" Immunol. Cell Biol. 2004, 82, 506-516.
Jegerlehner, A.; Storni, T.; Lipowsky, G.; Schmid, M.; Pumpens, P.; Bachmann, M. F. "Regulation of IgG antibody responses by epitope density and CD21-mediated costimulation" Eur. J. Immunol. 2002, 32, 3305-3314.
Kanchan, V.; Panda, A. K. "Interactions of antigen-loaded polylactide particles with macrophages and their correlation with the immune response" Biomaterials 2007, 28, 5344-5357.
Link, A.; Zabel, F.; Schnetzler, Y.; Titz, A.; Brombacher, F.; Bachmann, M. F. "Innate Immunity Mediates Follicular Transport of Particulate but Not Soluble Protein Antigen" J. Immunol. 2012, 188, 3724-3733.
Abstract of Service, R. F. "Biofuels and City Air: A Marginal Effect." Sci. 2012, 336, 292-293.
Prashant, C. K.; Bhat, M.; Srivastava, S. K.; Saxena, A.; Kumar, M.; Singh, A.; Samim, M.; Ahmad, F. J.; Dinda, A. K. "Fabrication of nanoadjuvant with Poly-ϵ-caprolactone (PCL) for developing a single-shot vaccine providing prolonged immunity" Int. J. Nanomedicine 2014, 12, 937-950.
O'Hagan, D. T.; Singh, M. "Advances in vaccine adjuvants" Expert Rev. Vaccines 2003, 2, 269-283.
Carcaboso, A. M.; Hernandez, R. M.; Igartua, M.; Rosas, J. E.; Patarroyo, M. E.; Pedraz, J. L. "Potent, long lasting systemic antibody levels and mixed Th1/Th2 immune response after nasal immunization with malaria antigen loaded PLGA microparticles" Vaccine 2004, 22, 1423-1432.
Ochsenbein, A. F.; Zinkernagel, R. M. "Natural antibodies and complement link innate and acquired immunity" Immunol. Today 2000, 21, 624-630.
Cuenca, A. G.; Jiang, H.; Hochwald, S. N.; Delano, M.; Cance, W. G.; Grobmyer, S. R. "Emerging Implications of Nanotechnology on Cancer Diagnostics and Therapeutics" Cancer 2006, 107, 459-466.
Ziv, O.; Avtalion, R. R.; Margel, S. "Immunogenicity of bioactive magnetic nanoparticles: Natural and acquired antibodies" J. Biomed. Mater. Res. A. 2008, 85, 1011-1021.

* cited by examiner

Zeta Potential (mV)

OVA pHEMA-py-OVA

| Gel Idx/Pos | 1/A1 | Instr./Gel Origin | AK275/Wang_Qian | Process Status | Analysis Succeeded |
|---|---|---|---|---|---|
| Plate [#] Name | [1] Protein | Instrument Sample Name | | Spectra | 11 |

| Rank | Protein Name | Species | Accession No. | Protein MW | Protein PI | Protein Score | Protein Score C. I. % | Total Ion Score | Total Ion C. I. % |
|---|---|---|---|---|---|---|---|---|---|
| 1 | Circumsporozoite protein OS=Plasmodium falciparum PE=3 SV=1 | | CSP_PLAFA | 44393.7 | 5.18 | 366 | 100 | 295 | 100 |

Peptide Information

| Calc. Mass | Obsrv. Mass | ± da | ± ppm | Start Seq. | End Seq. | Sequence | Ion Score | C. I. % | Modification | Rank | Result Type |
|---|---|---|---|---|---|---|---|---|---|---|---|
| 930.5043 | 930.4384 | -0.0659 | -71 | 330 | 336 | HIEQYLK | 19 | 0 | | | Mascot |
| 930.5043 | 930.4384 | -0.0659 | -71 | 330 | 336 | HIEQYLK | | | | | Mascot |
| 1303.5873 | 1303.5232 | -0.0641 | -49 | 98 | 108 | DDNNEDNEKLR | 19 | 0 | | | Mascot |
| 1303.5873 | 1303.5232 | -0.0641 | -49 | 98 | 108 | DDNNEDNEKLR | | | | | Mascot |
| 1372.6451 | 1372.5667 | -0.0784 | -57 | 307 | 319 | NVDENANANNAVK | | | | | Mascot |
| 1372.6451 | 1372.5667 | -0.0784 | -57 | 307 | 319 | NVDENANANNAVK | | | | | Mascot |
| 1382.5958 | 1382.515 | -0.0808 | -58 | 371 | 381 | DELDYENDIEK | | | | | Mascot |
| 1761.7019 | 1761.6156 | -0.0863 | -48 | 71 | 87 | SLGENDDGNNNNGDNGR | 38 | 0 | | | Mascot |
| 1761.7019 | 1761.6156 | -0.0863 | -48 | 71 | 87 | SLGENDDGNNNNGDNGR | | | | | Mascot |
| 1863.7899 | 1863.7029 | -0.087 | -47 | 290 | 306 | NNQGNGQGHNMPNDPNR | 30 | 36.332 | | | Mascot |
| 1863.7899 | 1863.7029 | -0.087 | -47 | 290 | 306 | NNQGNGQGHNMPNDPNR | | | | | Mascot |
| 1879.7848 | 1879.7012 | -0.0836 | -44 | 290 | 306 | NNQGNGQGHNMPNDPNR | 8 | 0 | Oxidation (M)[11] | | Mascot |
| 1879.7848 | 1879.7012 | -0.0836 | -44 | 290 | 306 | NNQGNGQGHNMPNDPNR | | | Oxidation (M)[11] | | Mascot |
| 2071.969 | 2071.8666 | -0.1025 | -49 | 320 | 336 | NNNNEEPSDKHIEQYLK | 185 | 100 | | | Mascot |

*Fig. 5*

Anti-DV2EP Specific IgG Titer
15000
10000
5000
0
DV2EP
PCL-py-DV2EP
**
**
Day 0
Day 14
Day 28
Day 42

*Fig. 7b*

POLYMER-PROTEIN CORE-SHELL PARTICLES AS EFFECTIVE VACCINE DELIVERY VEHICLES AND TREATMENTS METHODS USING THE SAME

PRIORITY INFORMATION

The present application claims priority to U.S. Provisional Patent Application Ser. No. 62/287,035 titled "Polymer-Protein Core-Shell Particles as Effective Vaccine Delivery Vehicles" of Wang, et al. filed on Jan. 26, 2016, the disclosure of which is incorporated by reference herein.

BACKGROUND

Generally, the immune system could be provoked by a variety of natural antigens. It is found that some biological particulate structures have the excellent effect on regulating and controlling the immune responses against the antigens presented on them, which then promotes the process of protective immunity. To enhance the immune-responses of a specific antigen, the size, repetitive structure, epitope density and multivalency are the important factors and all play significant roles. Currently, more and more scientists are interested in the application of polymer-based particles to deliver vaccines due to their potential immune-modulatory features.

SUMMARY

Objects and advantages of the invention will be set forth in part in the following description, or may be obvious from the description, or may be learned through practice of the invention.

A polymer-protein core-shell nanoparticle is generally provided. In one embodiment, the polymer-protein core-shell nanoparticle includes a pyridinyl group grafted polymer assembled with a protein or a glycoprotein based antigen to form a core-shell particle.

A method is also generally provided for treating an infected organism. In one embodiment, the method includes administering the polymer-protein core-shell nanoparticle to the infected organism.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIGS. 2*c* and 2*d* showing, respectively, the size distribution and zeta potential from DLS measurement; and FIGS. 2*e* and 2*f* showing, respectively, protein ultraviolet and visible detection and CD spectra for OVA solution and pHEMA-py-OVA.

FIG. 5 shows the mass spectrum result for CS27IVC after searching in database. The identified protein was Circumsporozoite protein from *Plasmodium falciparum* with molecular weight of 44393.7 and pI of 5.19, which were consistent with theoretical values.

FIGS. 7*a* and 7*b* shows the PCL-py-based PPCS-NPs promoted higher antibody responses comparing with the soluble proteins of malaria and dengue, respectively. *$p<0.05$; **$p<0.01$.

DEFINITIONS

Figure 1A:
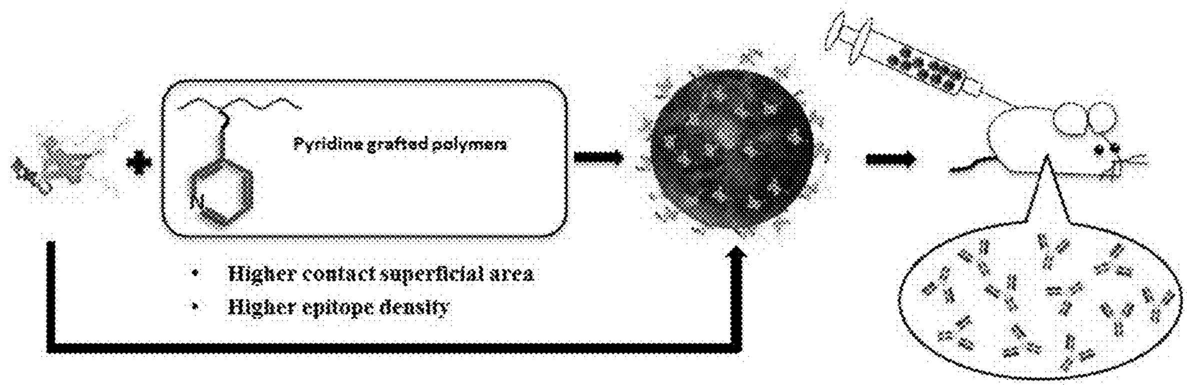
FIG. 1A is a schematic illustration of the self-assembly process of antigenic proteins and grafted polymers.
Figure 1B:
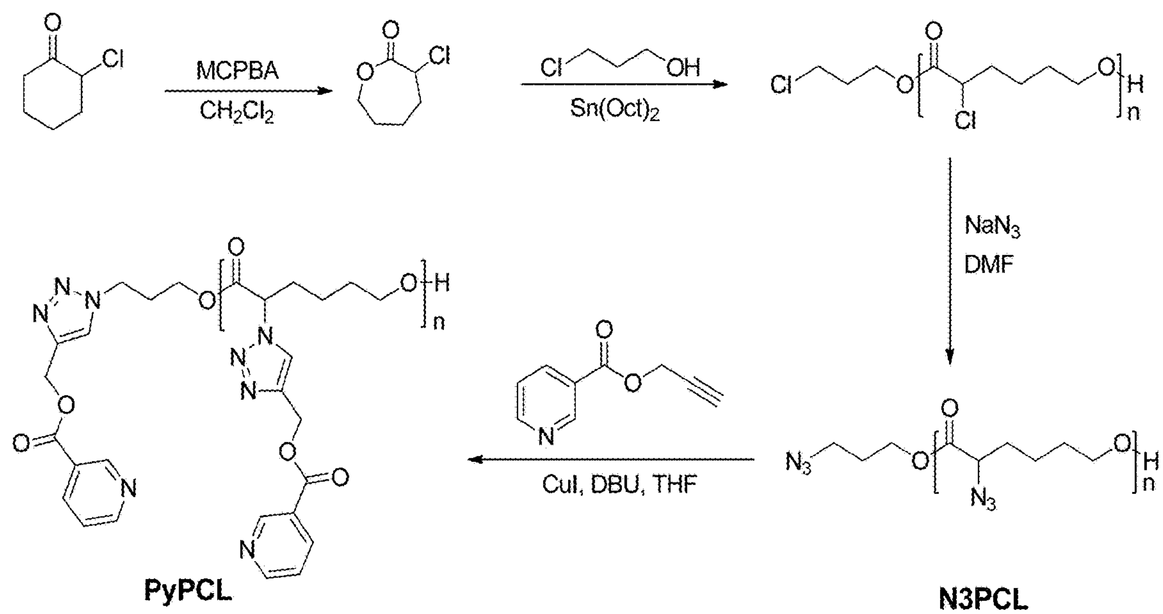
FIG. 1B is a schematic illustration of the synthesis of one exemplary embodiment: pyridine-grafted-poly(ε-caprolactone).

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale up to about 100 nm. For example, particles having an average diameter on the nanometer scale (e.g., from about 0.1 nm to about 100 nm) are referred to as "nanoparticles."

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The "weight average molecular weight" ($M_w$) is readily calculated by one of ordinary skill in the art, and generally refers to:

$$\overline{M}_w = \frac{\sum_i N_i M_i^2}{\sum_i N_i M_i}$$

where $N_i$ is the number of molecules of molecular weight $M_i$. The weight average molecular weight can be determined by light scattering, small angle neutron scattering (SANS), X-ray scattering, gel permeation chromatography, and sedimentation velocity.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A facile method is generally provided for preparing polymer-protein core-shell nanoparticles (PPCS-NPs) based on the self-assembly of functional proteins and these proprietary polymers. The resultant assemblies have well-controlled core-shell structures with high density protein components displayed as the corona. Furthermore, such PPCS-NPs were found to preserve protein activities and conformations. Such kind of assemblies could dramatically enhance the immune-responses of the protein-based antigens, likely due to the higher contact superficial area and higher epitope density platform, both of which are key attributes for generating robust IgG responses.

As shown in FIG. 1A, it has been discovered that a pyridinyl group grafted polymer can readily assemble with protein or glycoprotein based antigen to form a core-shell particle, where the polymer is the core and the protein displays as the corona. Some polymer examples include poly-4-vinylpyridine (P4VP), poly-2-vinylpyridine (P2VP), random or block copolymers with 2-vinylpyridine or 4-vinylpyridine units, pyridine grated poly(ε-caprolactone (PCL-py) and related copolymers, and pyridine grafted poly(2-hydroxyethyl)methacrylate (pHEMA-py), etc. The grafting groups can also be other heterocycles containing nitrogen and sulfur atoms.

These polymers can readily assemble with a variety of proteins and form core-shell structures. The pyridine and other grafting units have the ability to facilitate the self-assembly process, as well as to stable the final core-shell structures. It is also believed that co-assemblies with the proprietary polymers exhibited enhanced structural and molecular stabilities. Over 60 different enzymes, proteins and antibodies have been tested with this assembly technique.

It has been confirmed that a variety of antigens can be assembled in a similar manner. The assembly process is believed to be entropically driven, with electrostatic interaction and hydrogen bonding as "patches" to stabilize the final structures. The protein complexes acted as a mediator to minimize total interfacial energies between water and polymer. Proteins upon assembly demonstrated greater stability than enzyme alone. For prolonged storage, the assembled particles were flash frozen in liquid nitrogen, lyophilized overnight and the resulting powder was stored at ambient conditions (varied humidity, room temperature, exposure to light/air) for two weeks. The powder was reconstituted in water, and then analyzed by DLS for aggregates. The reconstituted particles resembled the original sizes with partial aggregate formations. The results from these studies provide strong evidence that the assemblies enhance the stability of the protein in solution and as lyophilized powder, which can be reconstituted prior to use.

More importantly, such protein/polymer assemblies promote strong IgG response from in vivo studies. It was found that the polymer/protein mixture is sufficient to generate a strong systemic IgG response against proteins.

A therapeutically effective amount of a PPCS-NPs of the invention is an amount of PPCS-NPs that enhances the immune-responses of the protein-based antigens, likely due to the higher contact superficial area and higher epitope density platform. For example, when present in a therapeutic or pharmaceutical composition, the amount of PPCS-NPs of the invention can be in the range of about 0.001% to about 35% by weight of the composition (e.g., about 0.5% to about 20% by weight of the composition). The therapeutically effective amount of PPCS-NPs necessarily varies with the route of administration. For example, a therapeutic amount between 30 to 112,000 μg per kg of body weight can be effective for intravenous administration.

However, the amount of the PPCS-NPs required will vary not only with the route of administration, but also the nature of the condition being treated and the age and condition of the patient and will be ultimately at the discretion of the attendant physician or clinician.

Useful dosages of the PPCS-NPs can be determined by correlating their in vitro activity, and in vivo activity in animal models described herein. The compound can conveniently be administered in unit dosage form; for example, containing about 0.001 μg to about 10 mg, conveniently about 0.01 μg to about 5 mg, more conveniently, about 0.10 μg to about 1 mg, and even more conveniently about 1.0 μg to 500 μg of PPCS-NPs per unit dosage form. The desired dose may be presented in a single dose, as divided doses, or as a continuous infusion. The desired dose can also be administered at appropriate intervals, for example, as two, three, four or more sub-doses per day. One of skill in the art can readily prepare and administer an effective formulation from available information using the teachings provided herein.

The PPCS-NPs of the invention can be formulated as pharmaceutical compositions and administered to a mammalian host, such as a human patient in a variety of dosage forms adapted to the chosen route of administration, i.e., orally or parenterally, by intravenous, intramuscular, topical or subcutaneous routes.

Thus, the PPCS-NPs may be systemically administered, for example, intravenously or intraperitoneally by infusion or injection. Solutions of the PPCS-NPs can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Examples

1. Preparation of Ovalbumin PPCS-NPs and Immune Response

In order to study the effect of core-shell nanoparticles on the immune response, glycoprotein ovalbumin was employed as a model protein to assemble with P4VP and pHEMA-py in the preliminary experiment.

Figure 2A:
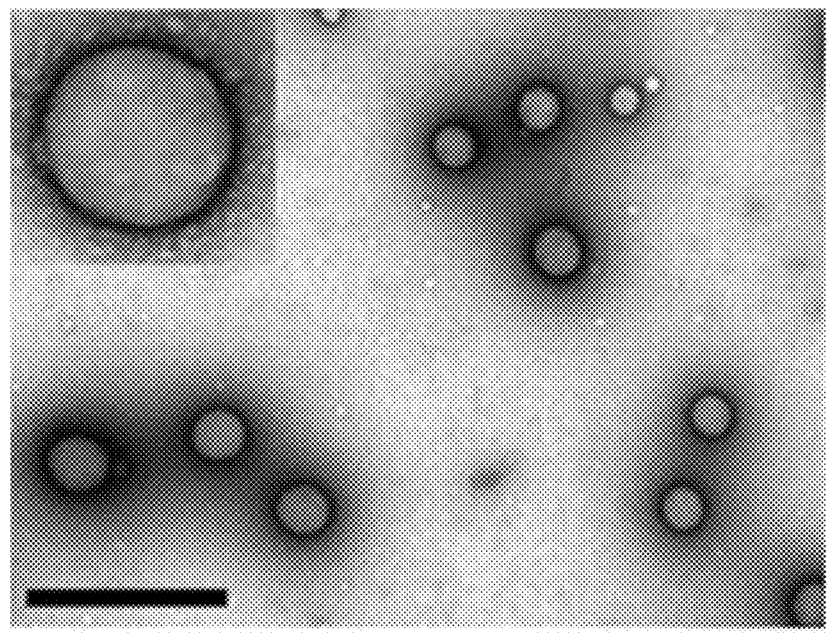
FIGS. 2*a*-2*f* shows the physicochemical characterization of pHEMA-py-OVA PPCS-NPs, with FIGS. 2*a* and 2*b* showing, respectively, TEM and FESEM images with the scale bar of 500 nm.
Figure 2B:
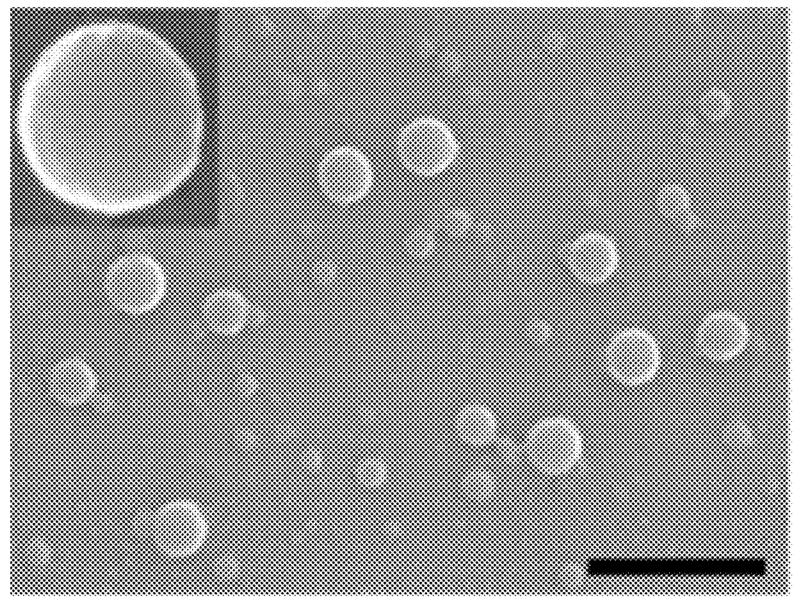
Figure 2C:
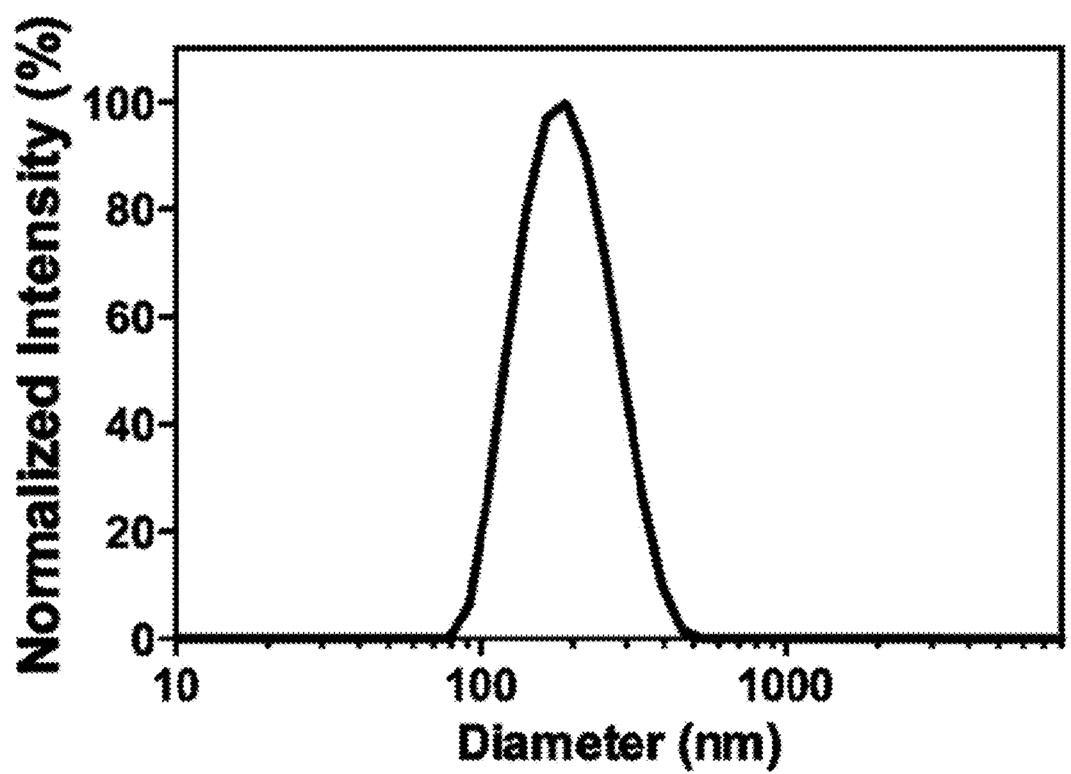
Figures 2D, 2E:
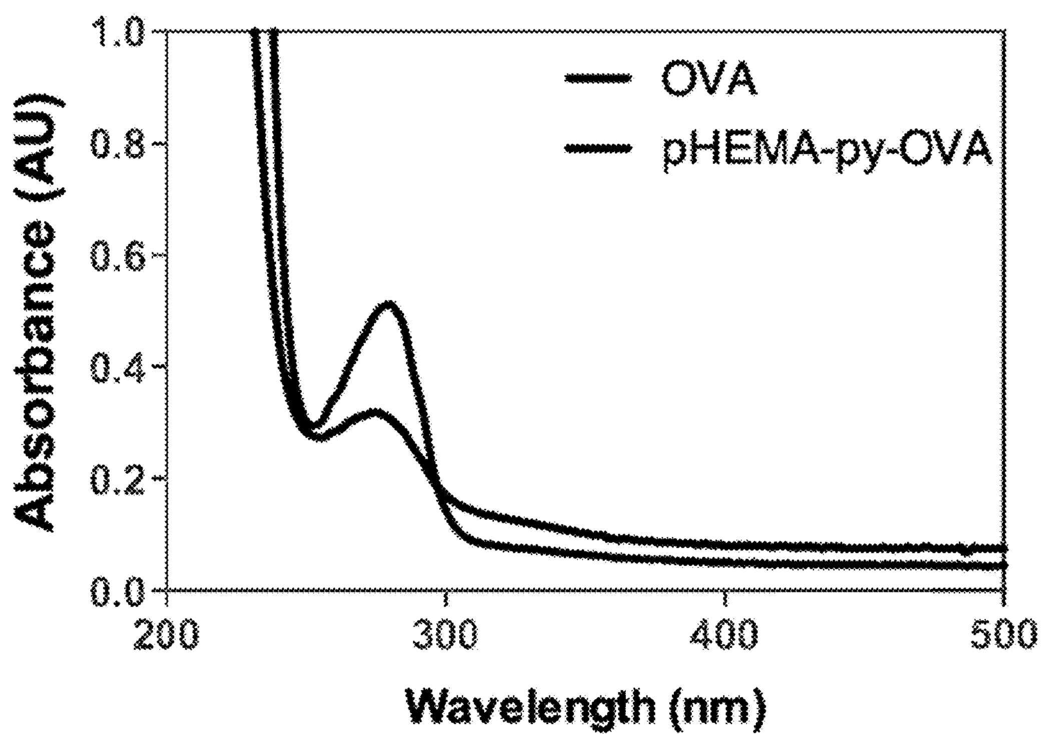
Figure 2F:
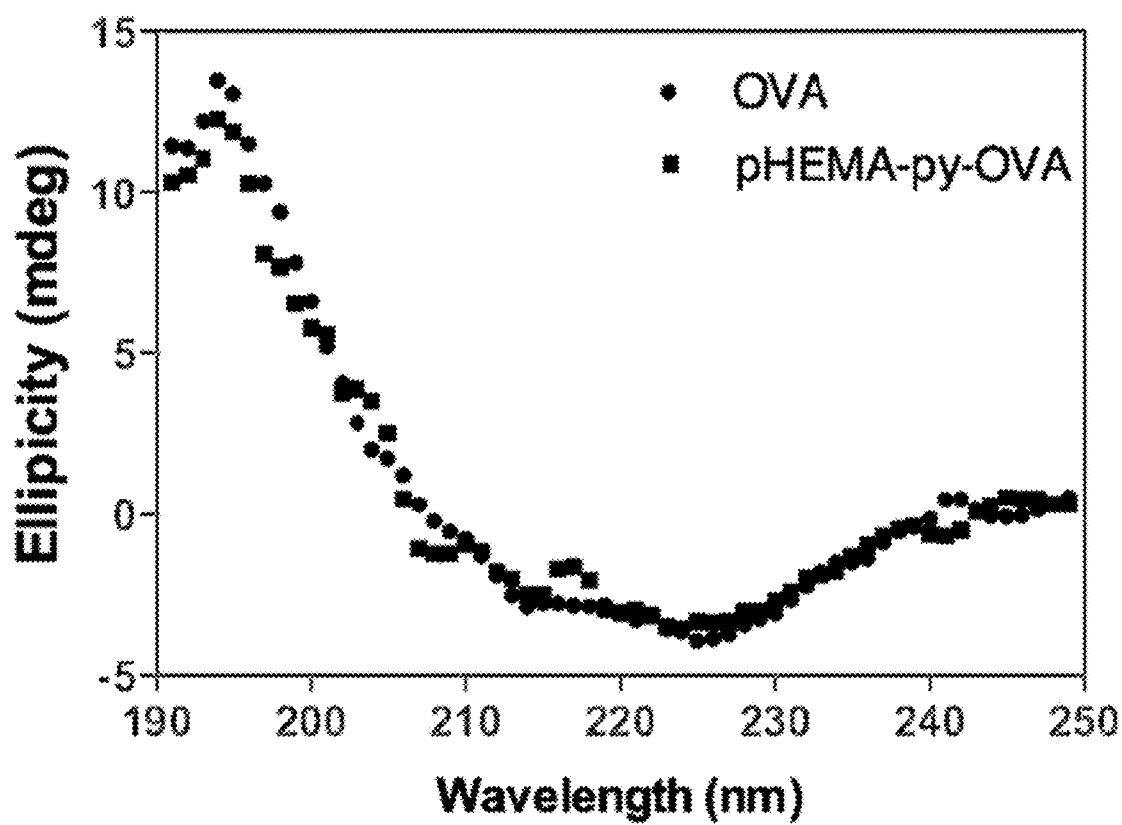

The formation of PPCS-NPs followed a reported method. Water was chosen to be as the reaction medium and the reaction was performed at pH 7.0 to keep the pyridine units from ionization. The assembling reaction was initiated by addition of pHEMA-py-DMF solution dropwise into the protein under gentle stirring. After removing the organic solvent by dialysis, the DLS showed the nanoparticles were around 200 nm diameter size with a low polydispersity index (PDI) of 0.02 (FIG. 2*c*). The resultant PPCS-NPs could maintain its morphology for over one month at room temperature. Transmission electron microscopy (TEM) and field emission scanning electron microscopy (FESEM) revealed the uniform spherical shape structures with a good smooth surface morphology (FIGS. 2*a* and *b*). Due to the small size of ovalbumin, it is hard to identify individual proteins on the NPs. The core-shell structures were also confirmed by zeta potential measurements. The zeta potential of ovalbumin solution was 13.7±0.5 mv, while the one of nanoparticles was 23.4±1.8 mv (FIG. 2*d*). In addition, circular dichroism (CD) and UV spectra revealed that the proteins still maintain the original folded conformations upon assembly (FIGS. 2*e* and *f*).

Figure 3:
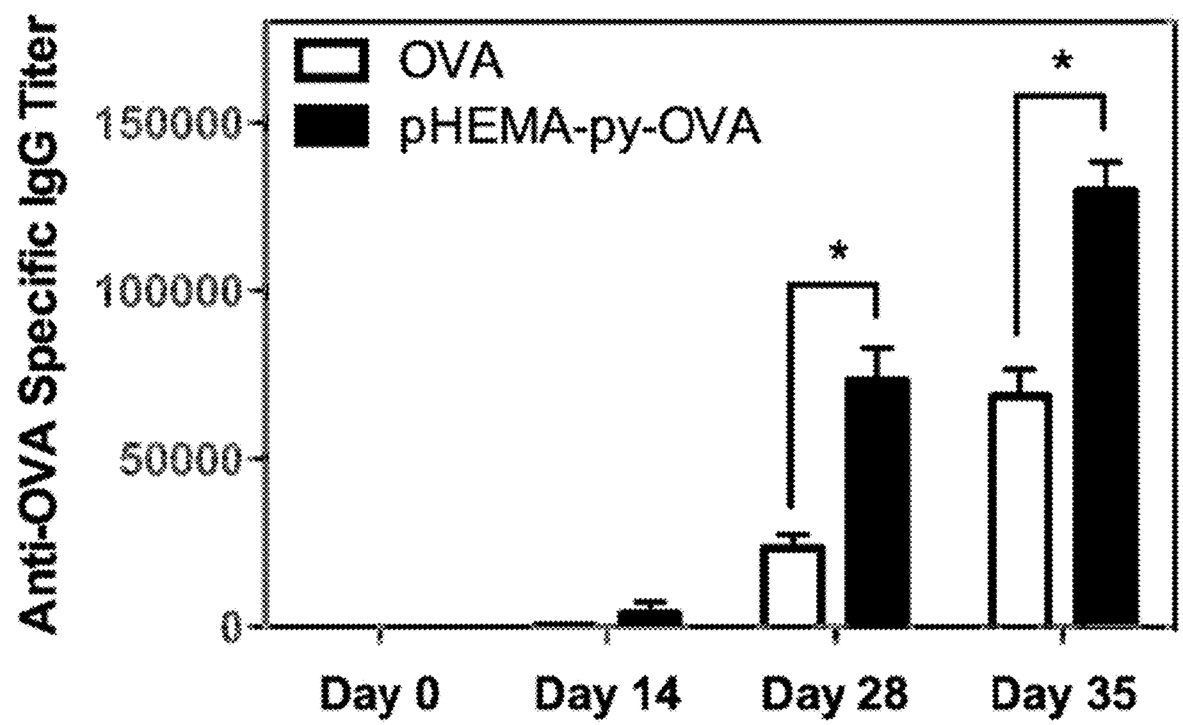
FIG. 3 shows the anti-OVA specific IgG titers in Balb/c mice after three subcutaneous immunizations with pHEMA-py-OVA PPCS-NPs and soluble OVA protein, respectively. *$p<0.05$, according to the Examples.

For immune-evaluation, 5 μg of ovalbumin in 100 μl of PBS was administered subcutaneously to each mouse (6-8 weeks old Balb/c mice) as controls. Two booster shots were given 14 days and 28 days after the first inoculation. For antigen/polymer, antigen concentration was determined by UV-Vis absorbance and protein quantification kit (Bio-rad). An equal amount of antigen was administered followed by two additional boosters 14 days and 28 days after the first injection. Serum samples were obtained by retro-orbital bleeding. Ovalbumin specific IgG titers were obtained by diluting antisera 3200-fold in 1×PBS-T (0.05% tween-20, 1% BSA) followed by serial dilutions. Overall, mice injected with ovalbumin alone had lower IgG titers in comparison to the mice injected with ovalbumin/polymer assemblies (FIG. 3).

2. PPCS-NPs Elicited Immune Response for Malaria and Dengue virus

Malaria and dengue are the most severe infectious diseases in the world, for which effective and usable vaccines are still not available, even though the continuous research and unremitting effort. The potential vaccine candidate for *Plasmodium falciparum* malaria targeting circumsporozoite protein (CS27IVC) and dengue virus serotype-2 envelope protein (DV2EP) as immunogens, respectively, were chosen.

Figure 4A:
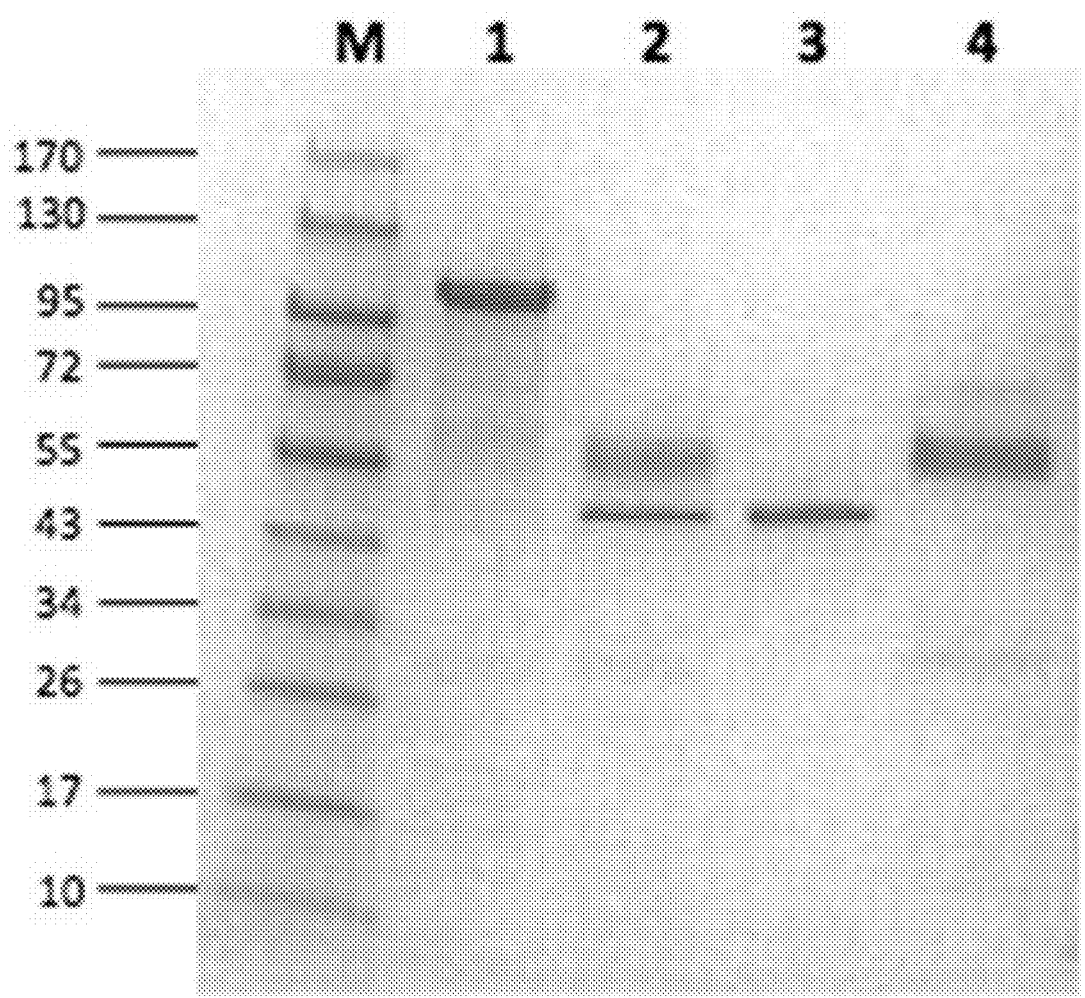
FIG. 4*a* shows a SDS-PAGE for *E. coli*-derived proteins after affinity purification. The M lane presents protein standard, while lane 1 for CS27IVC-MBP fusion protein, lane 2 for cleavage solution, lane 3 for flow-through and lane 4 for CS27IVC, according to the Examples.
Figure 4B:
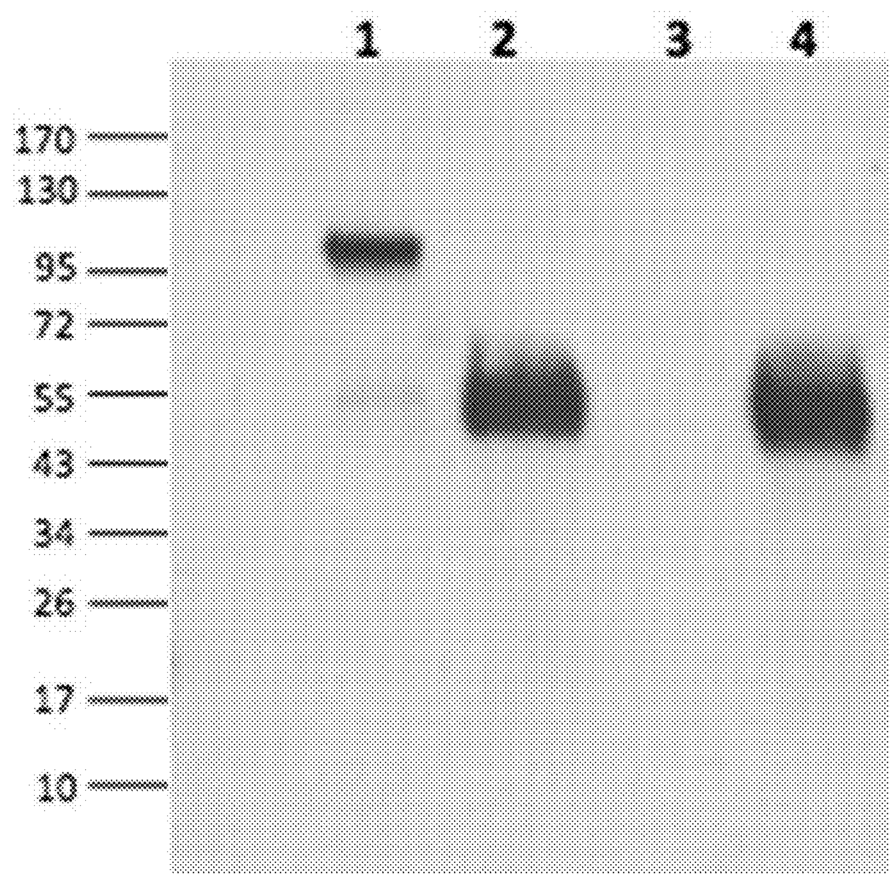
FIG. 4*b* shows a western blot for *E. coli*-derived proteins after affinity purification. The M lane presents protein standard, while lane 1 for CS27IVC-MBP fusion protein, lane 2 for cleavage solution, lane 3 for flow-through and lane 4 for CS27IVC, according to the Examples.

The *Escherichia coli* (*E. coli*)-derived recombinant DV2EP originated from dengue virus serotype 2, which has been proven to be more virulent comparing to the others. The protein was purchased from PROSPEC company (den-022). The recombinant *P. falciparum* CS protein CS27IVC (27-123(NANPNVDP)3(NANP)$_{21}$300-411), which contains region I, II and the repeat region, as well as several T cell epitopes for malaria, has been showed an immunodominant protective T cell antigen. In these experiments, CS27IVC was fusion expressed with maltose binding protein (MBP). After purification from *E. coli* cell lysate supernatants using Ni-NTA affinity chromatography, the CS27IVC was separated after being carved up by Factor xa. SDS-PAGE, western blot and mass spectrum analysis confirmed the purity and validity of the purified proteins (FIGS. 4 and 5). The endotoxin in both CS27IVC and DV2EP was less than 1 EU/mL.

Figure 6A:
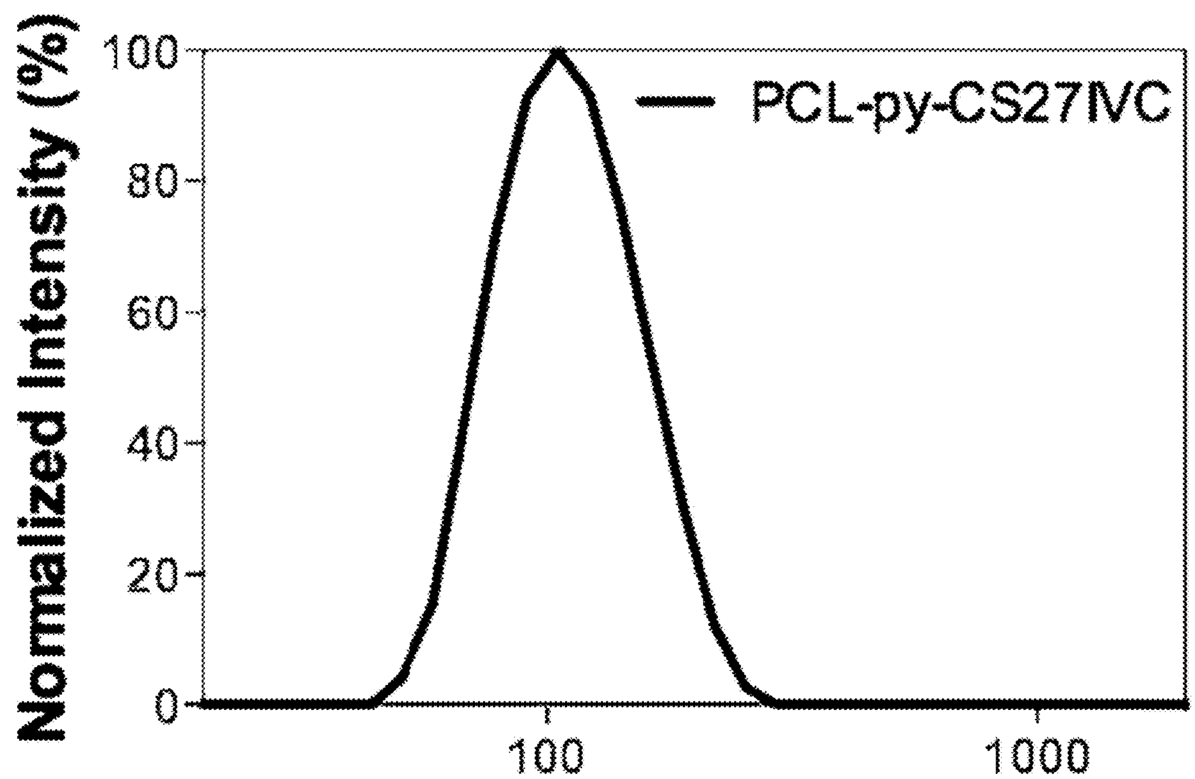
FIGS. 6*a*, 6*b*, and 6*c* shows the characterization of PCL-py-based PPCS-NPs for PCL-py-CS27IVC.
Figure 6B:
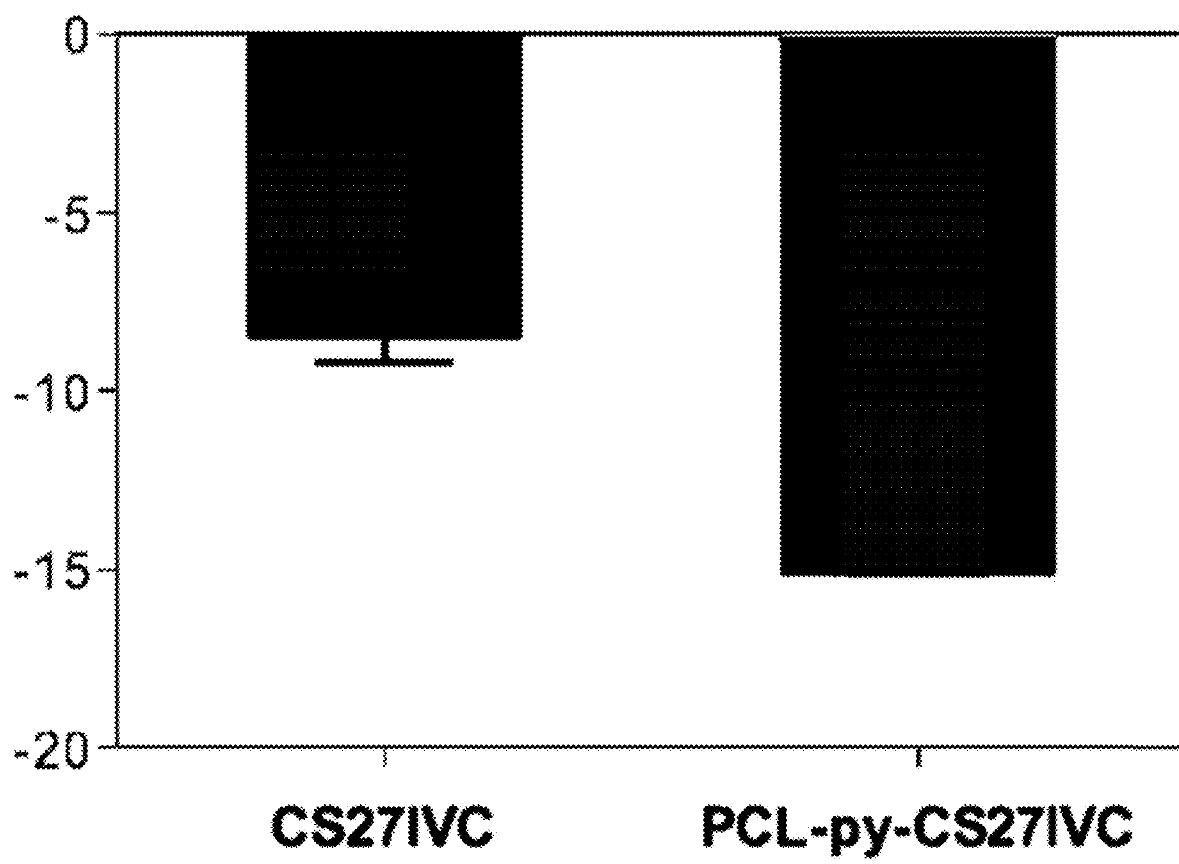
Figure 6C:
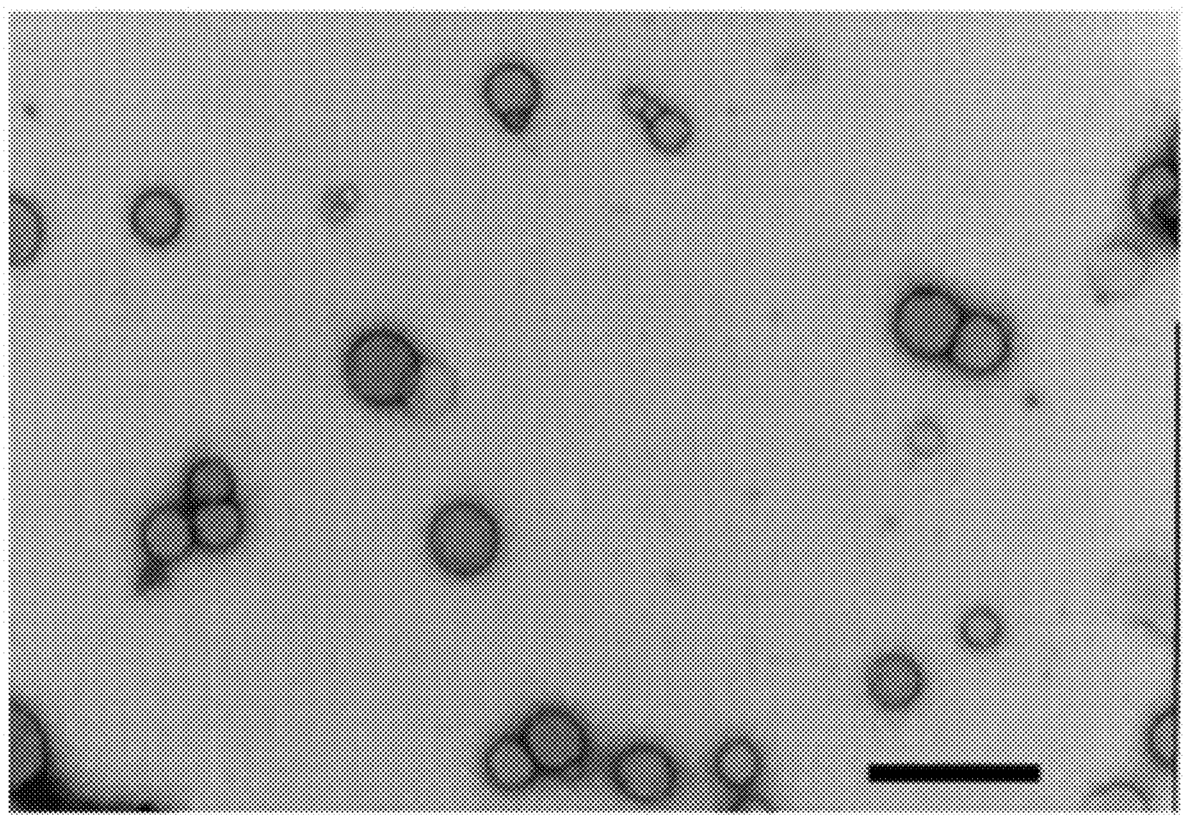
Figure 6D:
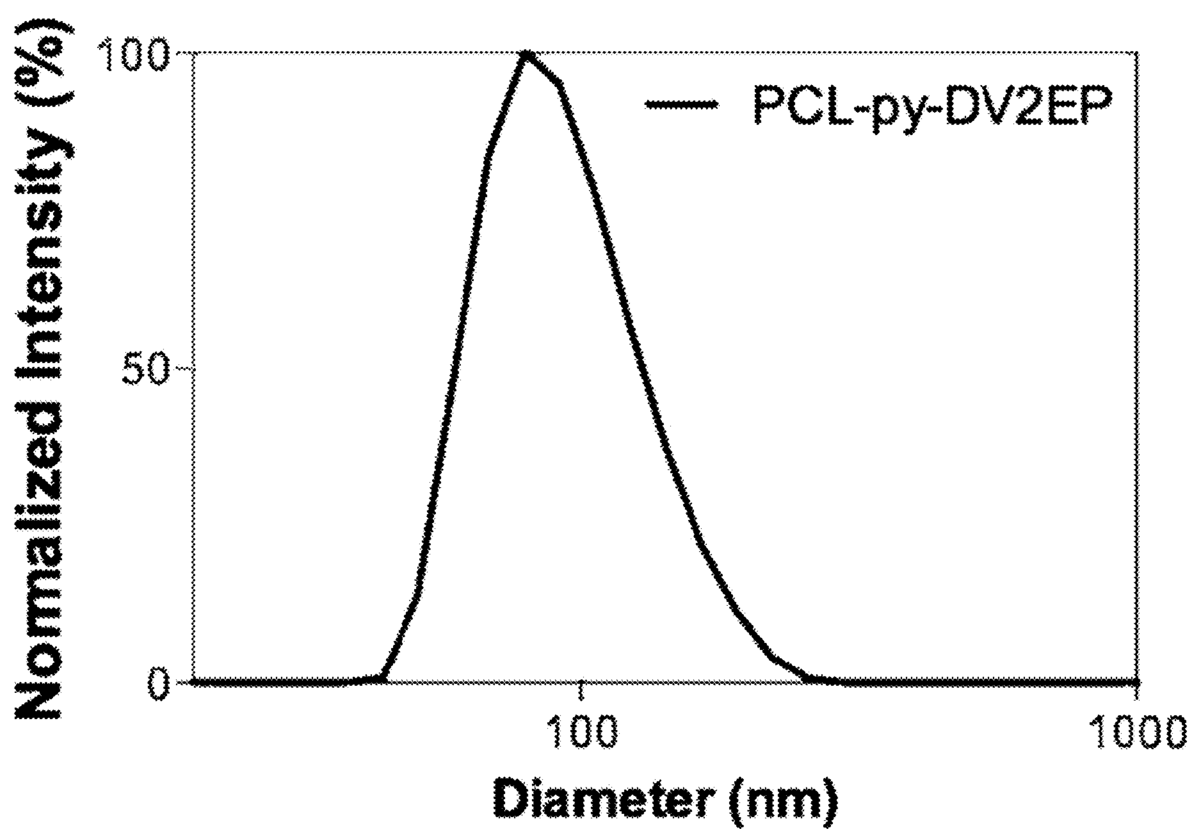
FIGS. 6*d*, 6*e*, and 6*f* shows the characterization of PCL-py-based PPCS-NPs for PCL-py-DV2EP. The size distribution from DLS measurement with PDI of 0.148 (a) and 0.161 (b), respectively. The zeta potential showed in (b) and (e) comparing with soluble proteins. TEM and FESEM images have the scale bar of 500 nm and 200 nm, respectively.
Figure 6E:
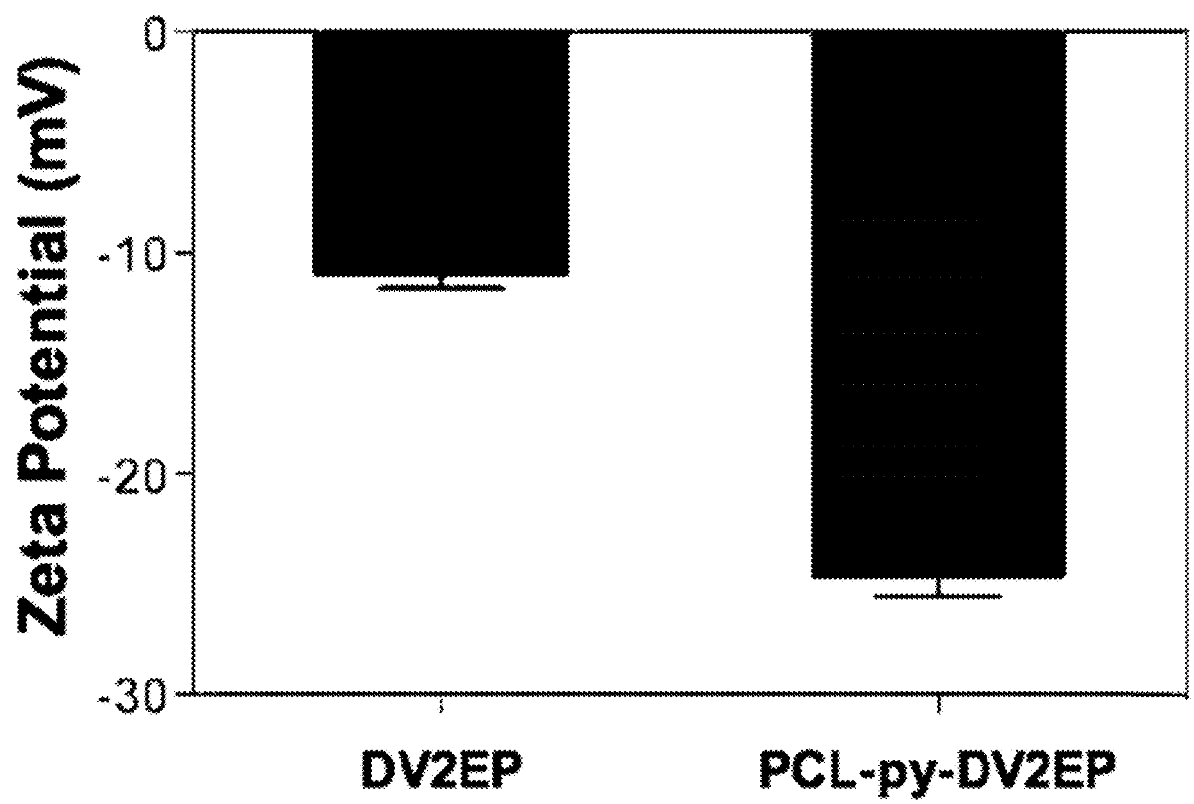
Figure 6F:
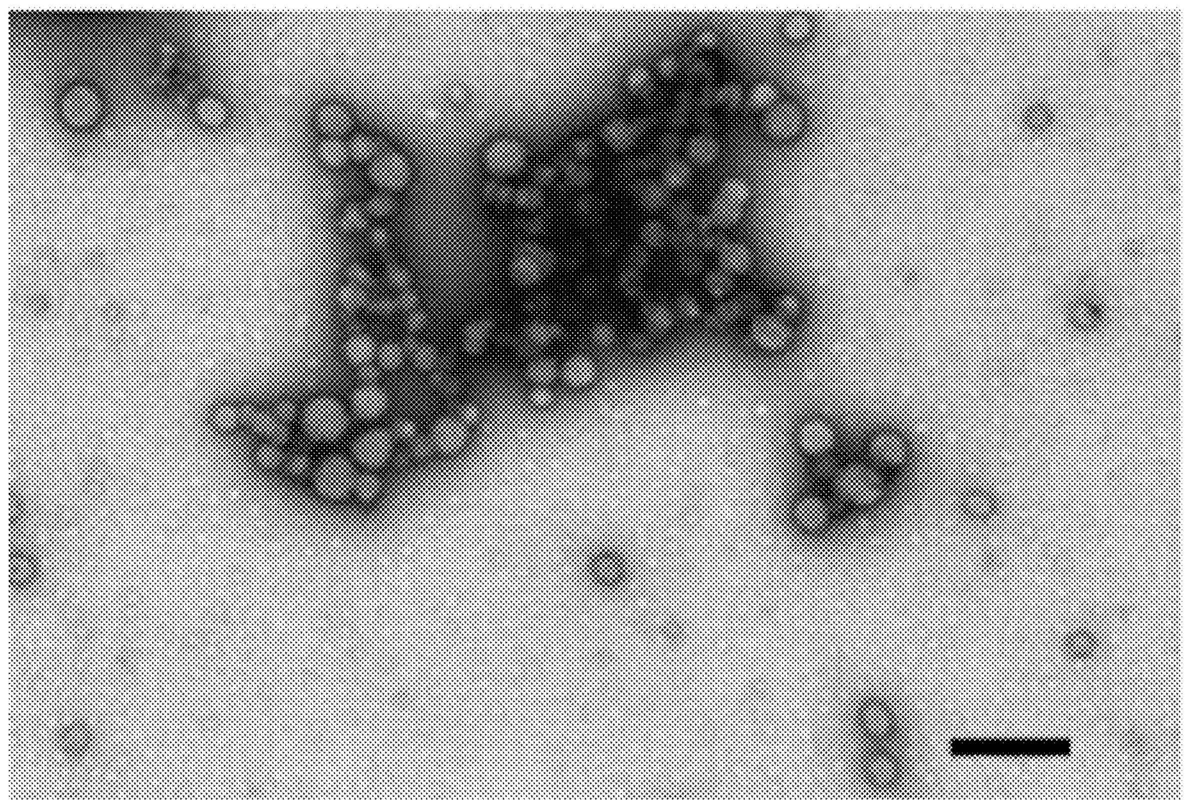

It has been reported that the nanoparticles in the size range of 100 nm can be processed by both dendritic cells (DCs) and macrophages, consequently stimulate the immune responses. PCL-py was employed for the assembly and in vivo experiments. Upon assembly, DLS showed the size of both PCL-py-CS27IVC and PCL-py-DV2EP nanoparticles were around 100 nm (FIGS. 6*a* and *d*), which was consistent with TEM results (FIGS. 6*c* and *f*).

Figure 7A:
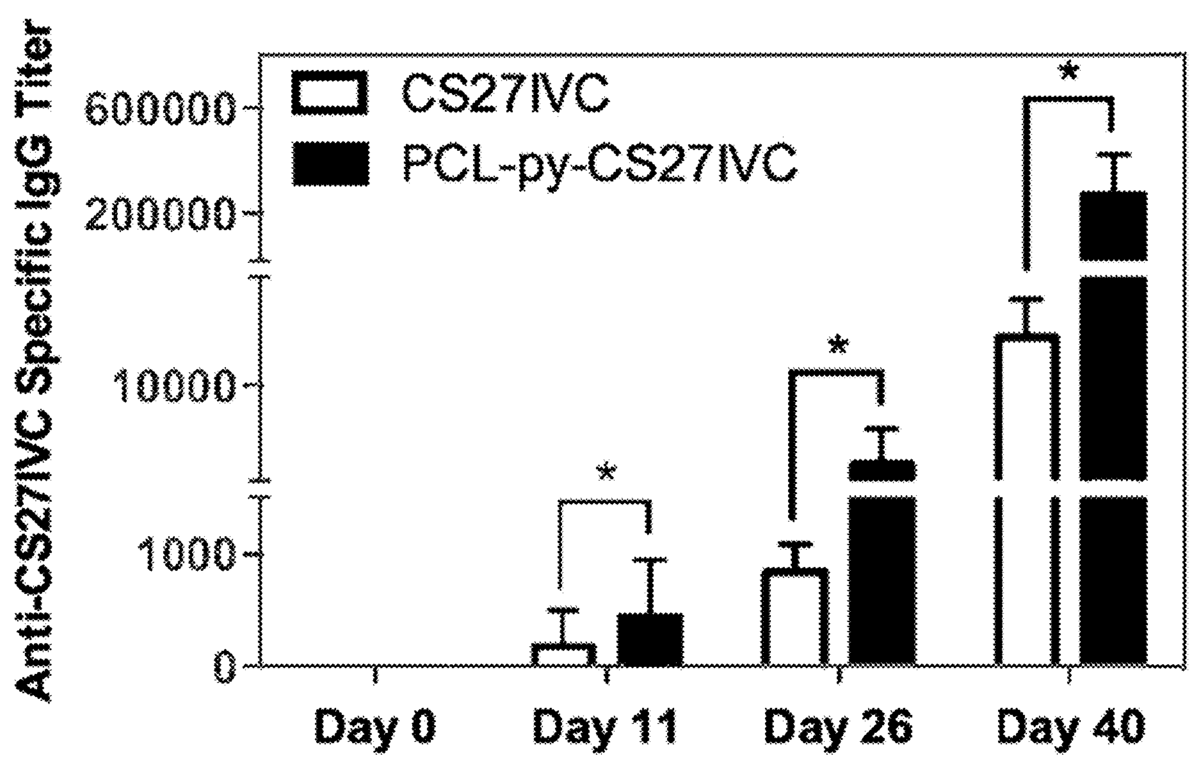
Figure 7B:
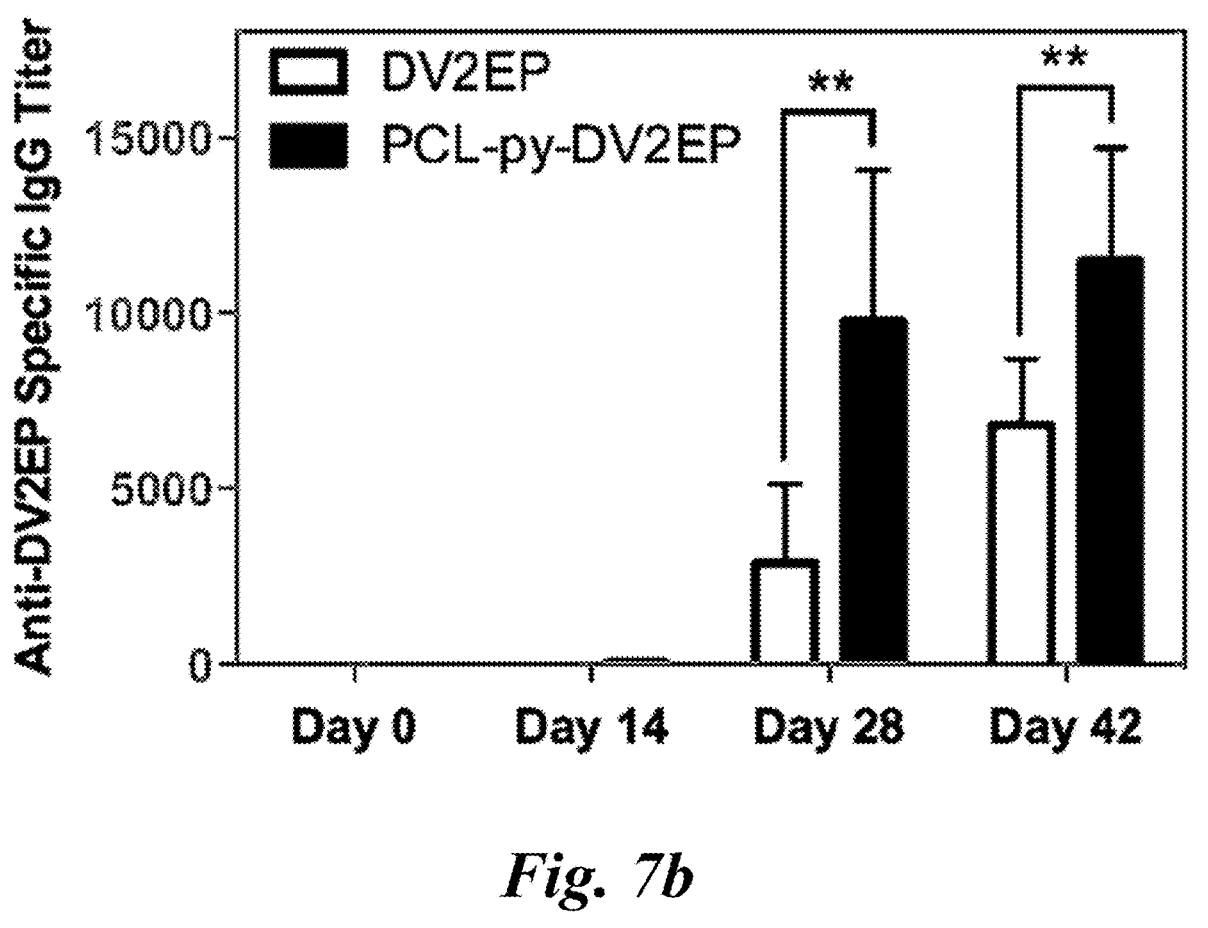

FIG. 7 shows the anti-CS27IVC and anti-DV2EP specific IgG responses evaluated by ELISA. Both nanoparticles started to elicit antibody response after the first immunization. Moreover, they showed significant higher titers than that from mice immunized with only proteins, indicating that PCL-py based presenting protein nanoparticles could efficiently stimulate the immune system and promoted a robust antibody response.

It was hypothesized that enhanced IgG responses observed with the particulate structures can be attributed to the higher surface areas of the particle structures. It could increase the protein density and would be the most important factor in its interaction with the immune cells. The spherical polymeric core-shell particle was an ideal structure for presenting immunogenic ligands that mainly depend on noncovalent interactions. Protein on particles presents a repetitive array of epitopes to B-cells and ensures prolonged contact of the antigen with immune cells. In addition, the appropriate size of nanoparticle could increase both the strength and quality of immune response.

Figure 8A:
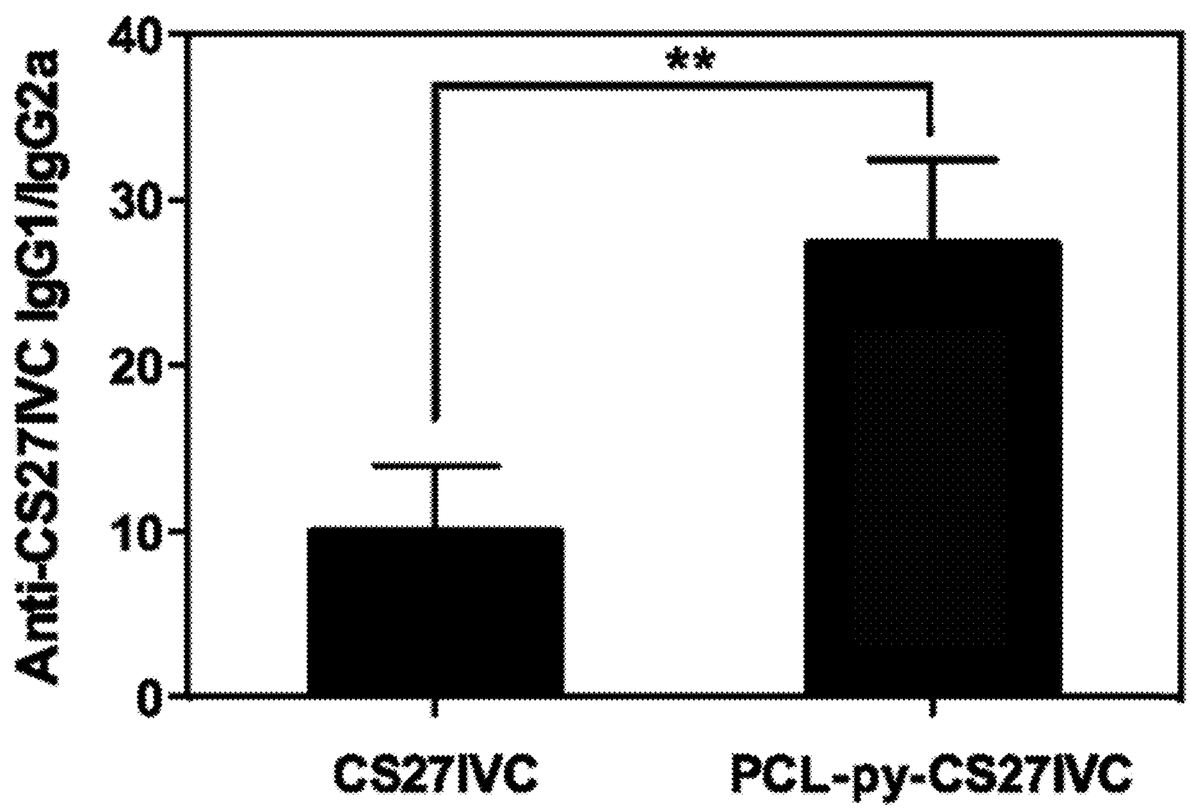
FIG. 8*a* shows the PCL-py-based PPCS-NPs increased higher IgG1 and IgG2a titer ratio comparing with the soluble proteins for CS27IVC, *$p<0.05$; **$p<0.01$.
Figure 8B:
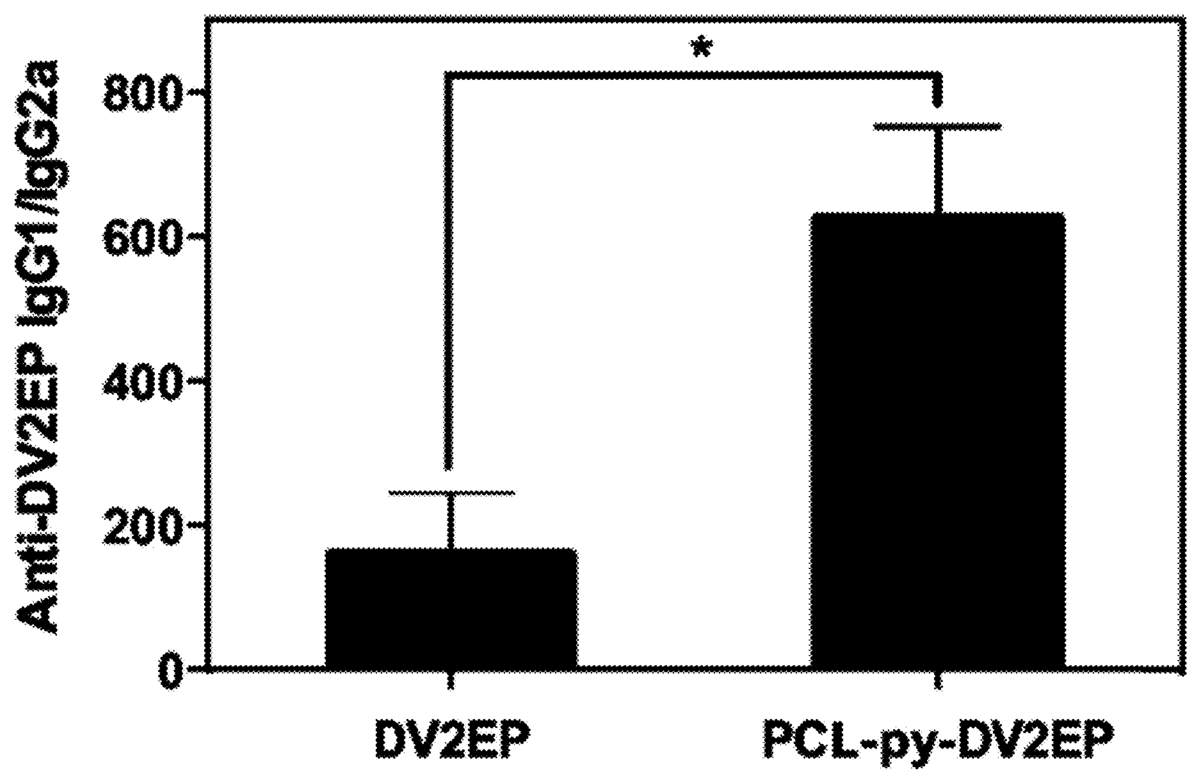
FIG. 8*b* shows the PCL-py-based PPCS-NPs increased higher IgG1 and IgG2a titer ratio comparing with the soluble proteins for DV2EP. *$p<0.05$; **$p<0.01$.

It is widely known that $IgG_1$ is an indicator of Th2-type response, which could promote cell-mediated immunity, whereas $IgG_{2a}$ prefers Th1-type response, which is related with humoral immunity. In order to evaluate the immune response pathway, the $IgG_1$ and $IgG_{2a}$ level in the immunized mice sera was detected. As shown in FIG. 8, both PCL-py-CS27IVC and PCL-py-DV2EP PPCS-NPs immunization resulted in a lower $IgG_1/IgG_{2a}$ ratio than that from protein immunization, which implied the potential ability of inducing cellular immune response of these PPCS-NPs. The result could be attributed to the capacity of the structures to deliver the antigen directly to T and B cells. This could upregulate higher levels of surface MHC class I (MHC I) molecules in comparison to MHC class II (MHC II) molecules, thus followed by activating both humoral and cellular responses.

3. In Vivo Nontoxic Characteristic of the PCL-py Based PPCS-NPs

An important concern of a polymeric particle vaccine delivery system is the potential toxicity, which can cause unnecessary inflammatory side effects and even more serious disease.

Figure 9A:
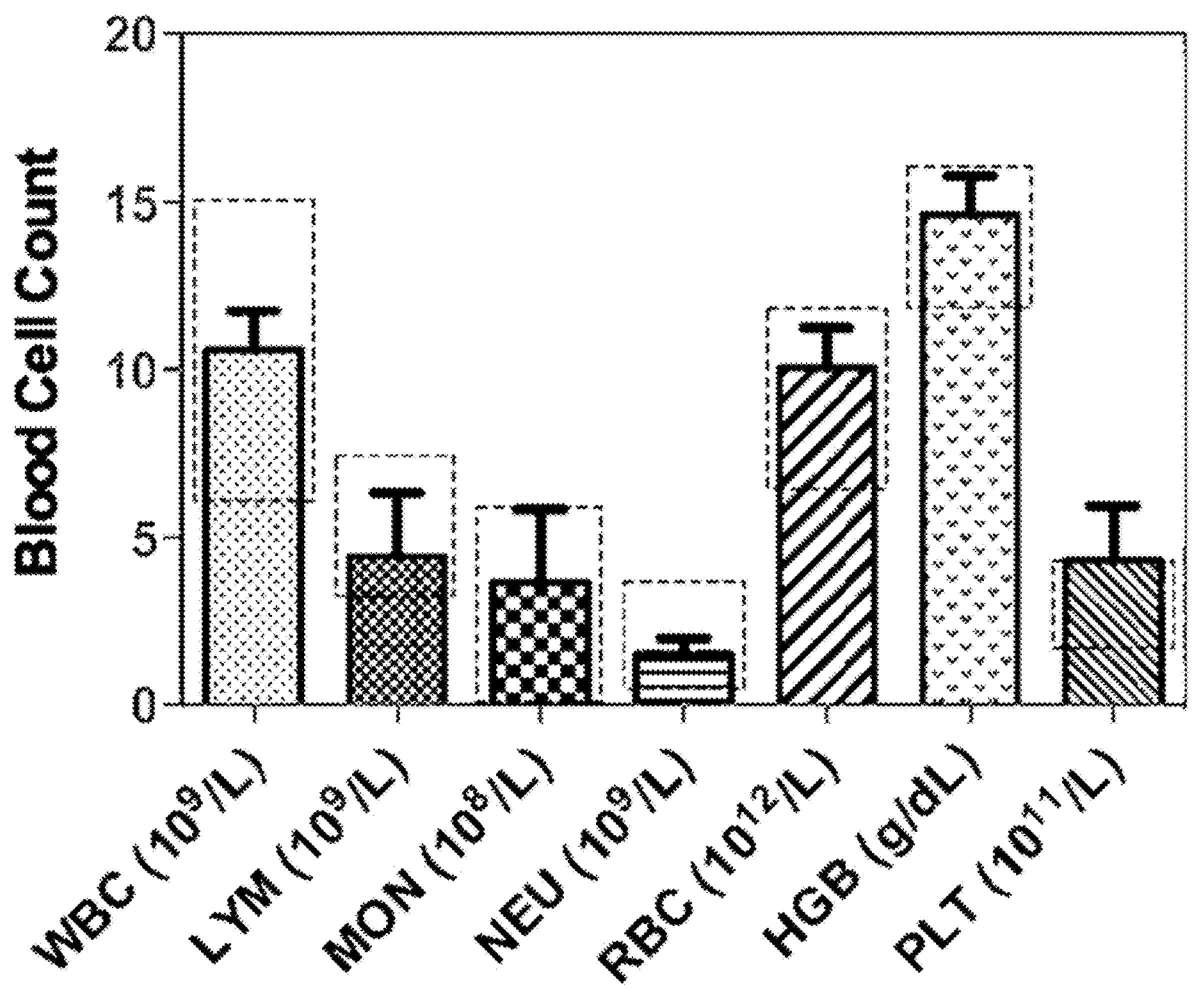
FIGS. 9*a*, 9*b*, and 9*c* show the blood cell count, mice body weight and normalized spleen weight were detected after three subcutaneous immunizations for CS27IVC.
Figure 9B:
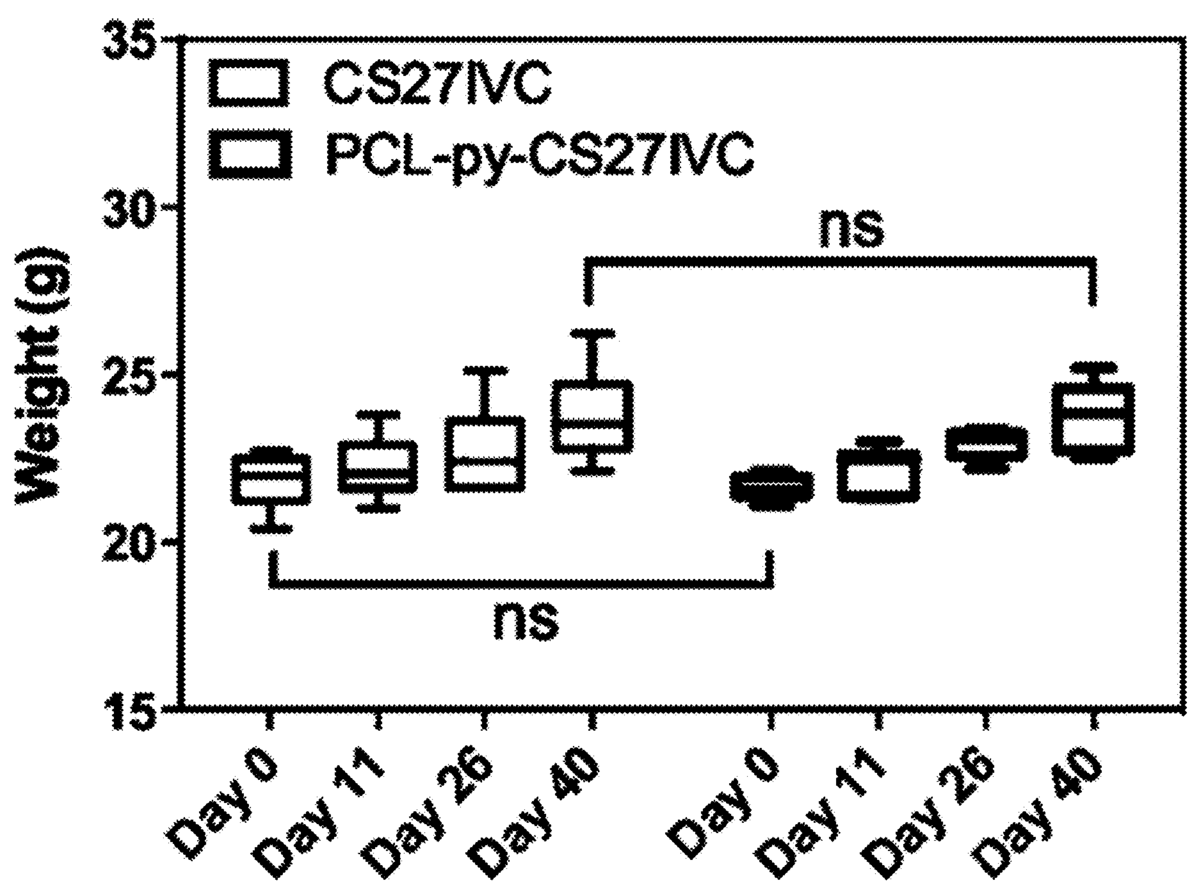
Figure 9C:
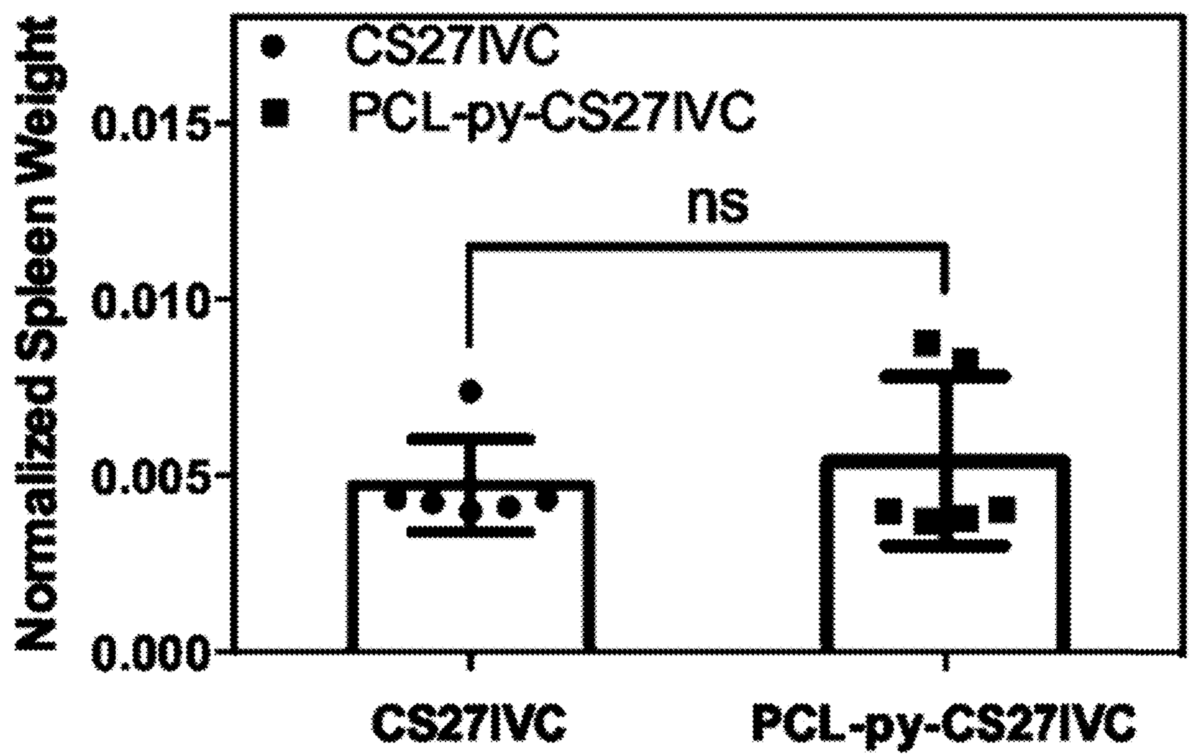
Figure 9D:
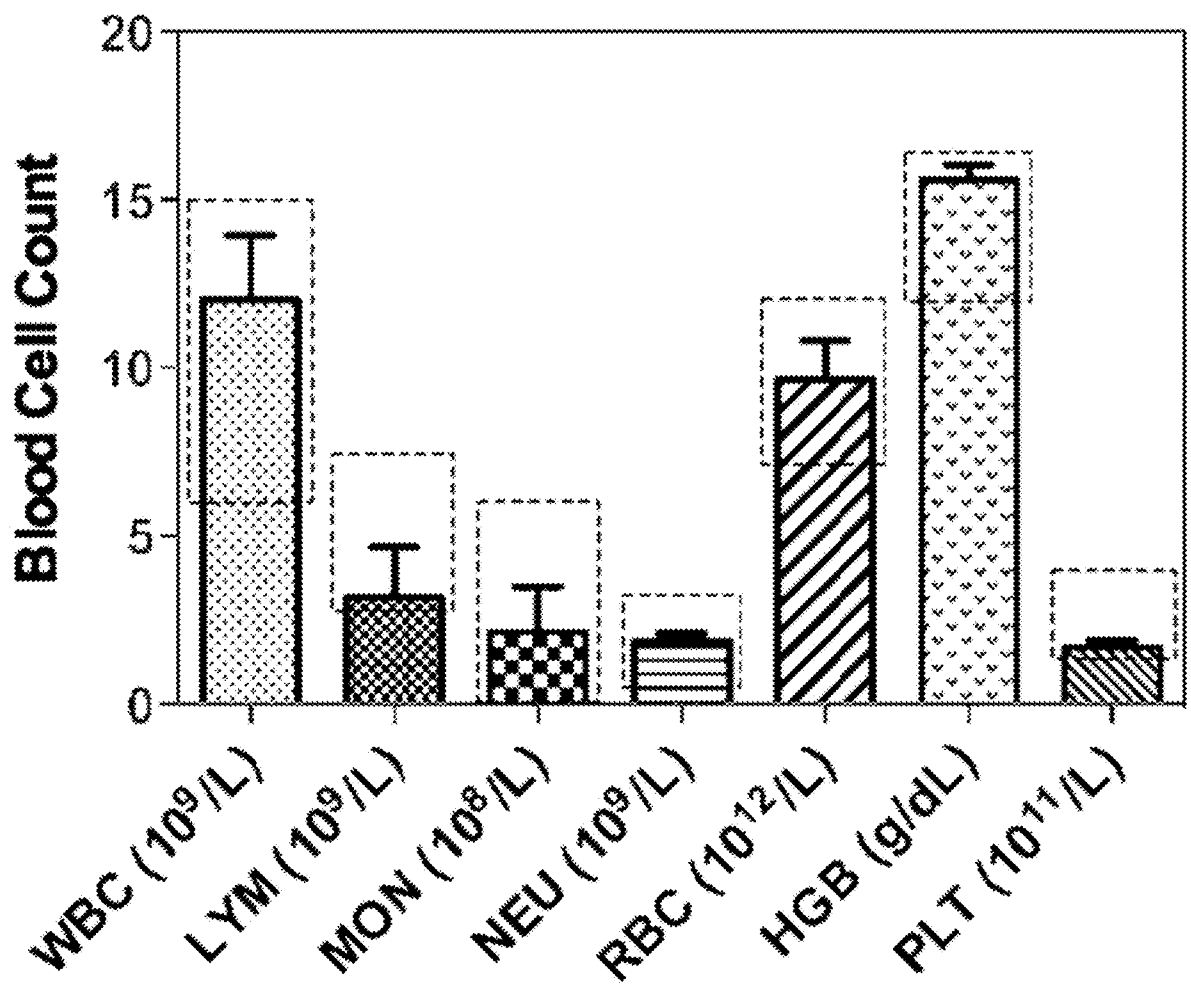
FIGS. 9*d*, 9*e*, and 9*f* show the blood cell count, mice body weight and normalized spleen weight were detected after three subcutaneous immunizations for DV2EP. The blood cell parameters included total white blood cells (WBC), lymphocyte (LYM), monocyte (MON), NEU (neutrophil), red blood cell (RBC), hemoglobin (HGB) and platelet (PLT), the red imaginary frames presented the normal range for each parameter. ns=not significant.
Figure 9E:
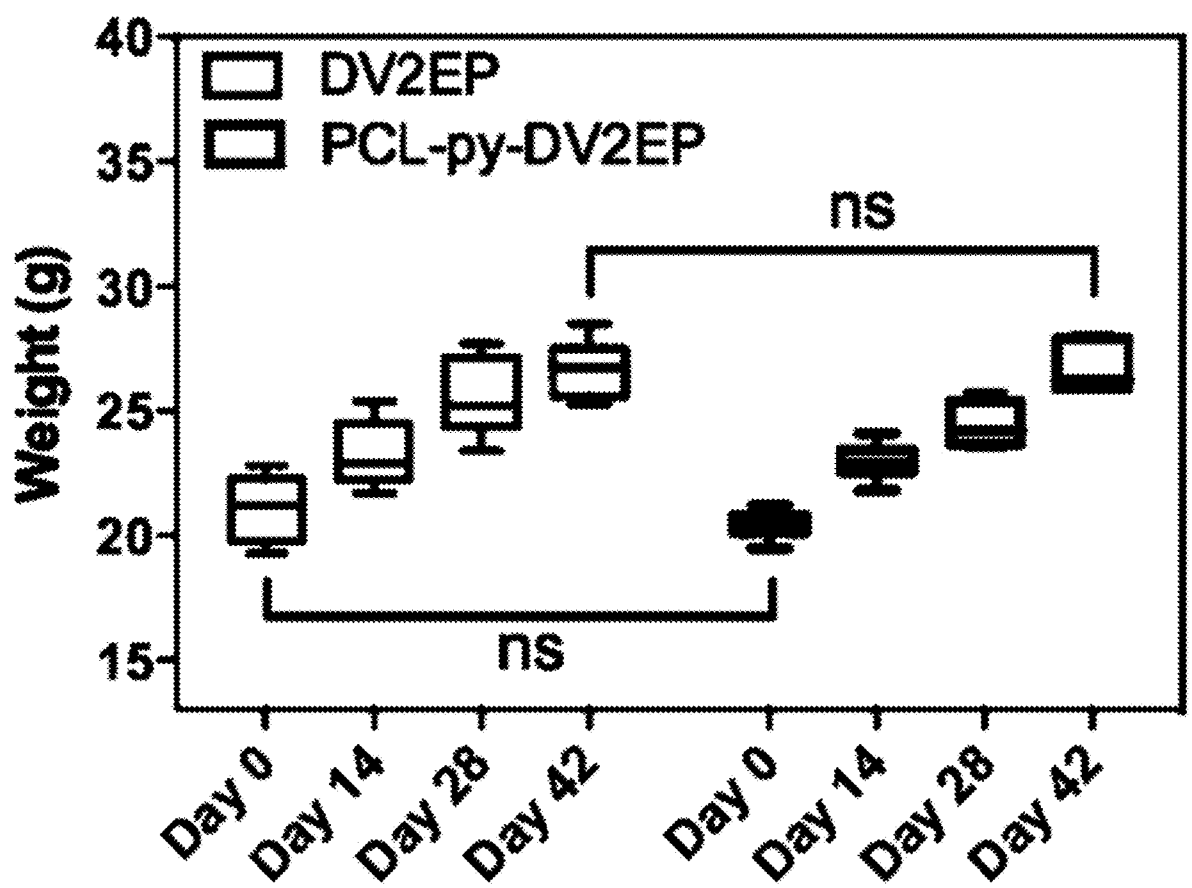
Figure 9F:
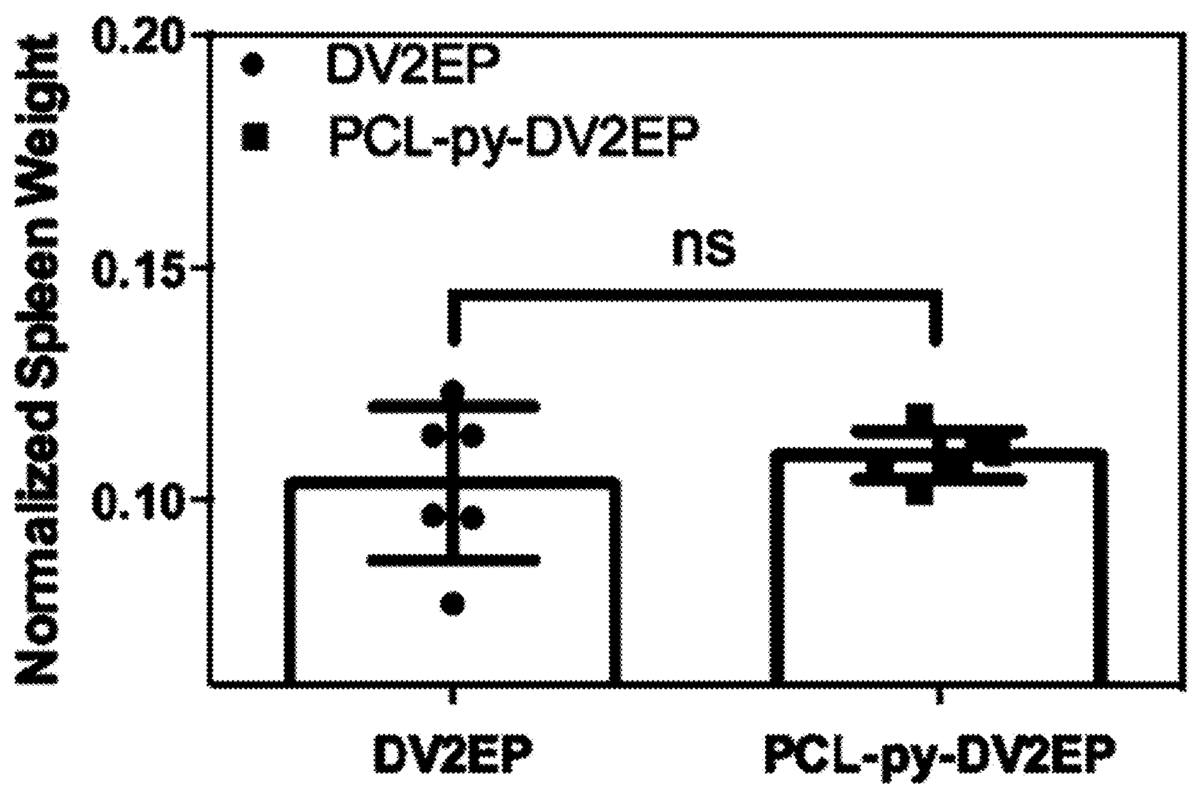

Regarding this, the toxicity of the PPCS-NPs was tested in vivo. Groups of six mice were immunized with the same amount of proteins or nanoparticles through the subcutaneous route. The blood samples from each mice group were analyzed for total blood count before each immunization. All the blood parameters, which indicate animal health including host inflammatory response, significant loss of blood and other abnormalities were shown to be in the normal range in all animals in each stage of immunization (FIGS. 9*a* and 9*d*). Animals were weighed before each immunization. As shown in FIGS. 9*b* and 9*e*, no significant weight change was observed between the two groups neither in CS27IVC or DV2EP project. At the end of the day time period, the mice were euthanized, the liver, lung, kidney and spleen were collected, and there was no obvious lesions or damages observed. The normalized weights of the spleen (organ weight/body weight) between the two groups were no significant difference (FIGS. 9*c* and 9*f*). These results indicated that immunization of the PCL-py-based nanoparticles could not cause any apparent signs of animal illness or diminished health.

Figure 10:
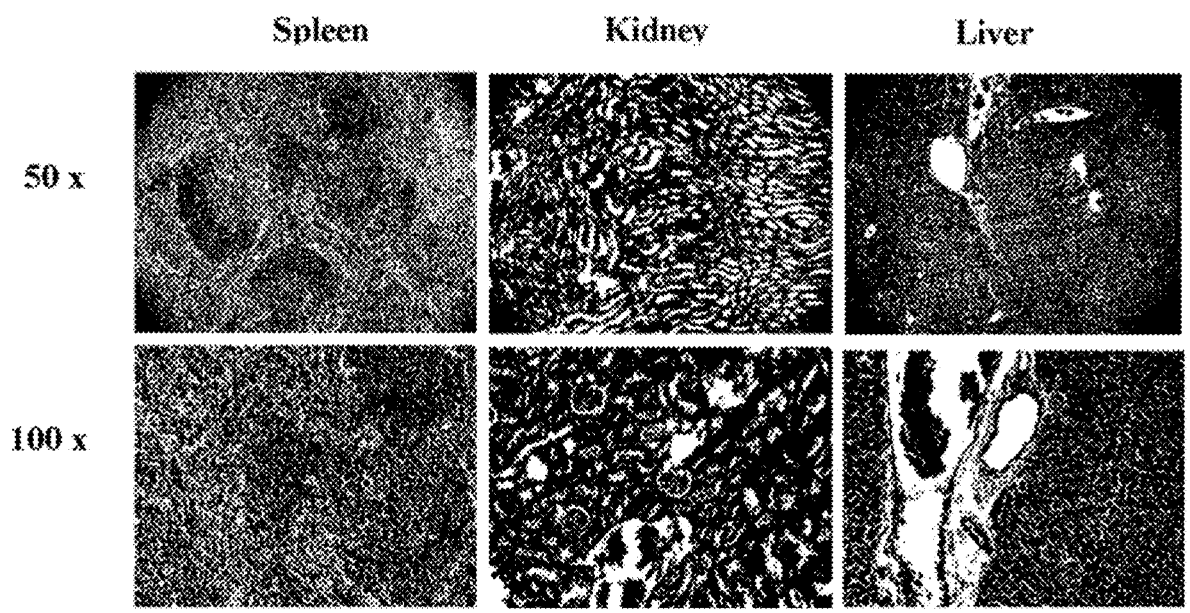
FIG. 10 shows the histological analysis of the effect of PCL-py-based PPCS-NPs administration on the microstructure of spleen, kidney, and liver at 50× and 100× magnifications.

PCL were used widely in the research of biomedicine and bioengineering due to its biodegradable and biocompatible property, which was consisting with these result. After preparing the histologic sections from the excised tissues, the effect of nanoparticles on the microstructure was evaluated. FIG. 10 shows the images of HE stained sections of the tissues, which suggested no obvious damage in the microstructure of the tissues was observed. These above results demonstrate that the PCL-py-based PPCS-NPs vaccine delivery system displayed no acute toxicity in vivo.

Supplemental Procedures

1. PPCS-NPs Preparation

The polymer-protein nanoparticles were prepared following the typical procedure reported previously. Briefly, the protein solution was prepared in water or buffer, which concentration was 60 μg/mL. The polymer ($M_w$ 38000) solution, which was prepared freshly in DMF (1.0 mg/mL) was dropwise added into the protein solution with appropriate stirring speed at RT. For pHEMA-py-OVA assembling, the final concentration of pHEMA-py was 200 μg/mL, while for PCL-py-CS27IVC and PCL-py-DV2EP assembling, the final concentration of PCL-py was 60 and 260 μg/mL. The samples were kept stirring at RT for at least 30 min and then dialyzed against corresponding liquid with a 3500 molecular weight cutoff dialysis tubing (Pierce) for 24 h at 4° C. to remove the organic solvent and changed the liquid three times.

2. PPCS-NPs Characterization

The size distributions and zeta potential were measured by using dynamic light scattering (DLS, Zetasizer Nano ZS, Malvern Instruments) without a further dilution or filtration. TEM analysis was performed by using a Hitachi H-8000 electron microscope. 100-mesh carbon-coated copper grid (plastic-side down) was placed on the 5 μL of liquid specimen drop for 10 min at RT. After wicking away excess fluid with filter paper, the grid was then stained with 10 μL of 2% uranyl acetate for 30 s and observed with the machine. The particle surface morphology was analyzed by using Ultraplus field emission scanning electron microscopy (FE-SEM), after coating the particle surface with gold-palladium over an aluminium stub. UV-vis absorption analysis was performed using the NanoDrop 2000 spectrophotometer (Thermo Scientific). Circular dichroism (CD) was performed by using a quartz cuvette with a 2 mm path length on a Jasco 815 spectrophotometer at a rate of 100 nm/min with a 1 nm step resolution and a 1 s response.

3. In Vivo Studies

The animal study procedures were performed after review and approval by the Institutional Animal Care and Use Committee of Medicine School in University of South Carolina. Six male Balb/c mice (about 6 to about 8 weeks old) for each group were immunized subcutaneously with 10 μg protein or PPCS-NPs (based on the protein concentration) per mouse. After the first immunization on day 0, two other immunizations were given on day 14 and day 28. The mice were performed retro-orbital bleeding and weighing before and after each immunization. Complete Blood Count (CBC) was preformed right after each blood withdrawal by using the ABAXIS VetScan HM5 Hematology Analyzer System. The blood were kept at 4° C. overnight and centrifuged at 3000 rpm for 10 min to obtain the upper serum for ELISA. The mice were euthanized after the final immunization. Mouse tissues including liver, lung, kidney and spleen were exteriorized and the weight of each spleen was recorded and normalized to the weight of the mouse. All the tissues were kept in 10% neutral buffered formalin for 72 h at 4° C. and then dehydrated and embedded in paraffin wax. The embedded paraffin wax were cut to slices and stained with hematoxylin and eosin (HE) stain for imaging. The slides were prepared, imaged and analyzed by School of Medicine in University of South Carolina.

4. ELISA 0.2 μg/mL protein in 1×PBS was coated in 96-well shape plates (Greiner Bio-One) (100 μL per well) for 12 h at RT. The plates were then washed twice with washing buffer (1×PBS, pH 7.4, 0.05% tween-20) and blocked with blocking buffer (1×PBS, pH 7.4, 0.05% tween-20, 1.5% BSA) for 1 h at RT. After removing the liquid, the plates were incubated with mouse sera, which were diluted 100 folds in the first well and four folds serial dilutions in the others for 1 h at RT. The plates were then washed twice with washing buffer and incubated with HRP-labeled goat anti-mouse IgG antibody at 10000 folds dilution for 1 h at RT. To determine the titer of $IgG_1$ and $IgG_{2a}$, HRP-labeled goat anti-mouse $IgG_1$ and $IgG_{2a}$ with the same dilution were used in place of IgG, respectively. The plates were washed four times with washing buffer and incubated with 3,3',5,5'-Tetramethylbenzidine solution (TMB; Amresco) for 20 min in dark. The reaction was stopped by adding 50 μL stop solution (0.2 M $H_2SO_4$) per well and measured at absorbance 450 nm. The titration curves were drawn up by Origin Pro v8.0 and the titers were determined as serum dilutions that gave mean optical density (OD) values three times greater than average background OD value.

5. Statistical Analysis

Statistical analysis was performed by using GraphPad Prism Software. Comparison between two groups was performed with t-test. Differences between PPCS-NPs immunized groups and protein immunized groups were considered statistically significant at $p<0.05$.

The abbreviations used herein are defined by CCR2 is CC chemokine receptor 2; CCL2 is CC chemokine ligand 2; CCR5 is CC chemokine receptor 5; and TLC is thin layer chromatography.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A vaccine comprising a plurality of polymer-protein core-shell nanoparticles, each of the nanoparticles comprising:

a pyridinyl group grafted polymer assembled with a protein based antigen to form a core-shell nanoparticle, wherein each of the nanoparticles has a surface comprising the protein based antigen noncovalently associated to one or more pyridinyl groups, wherein the protein based antigen comprises at least one protein selected from the group consisting of: a circumsporozoite protein and a dengue virus serotype-2 envelope protein.

2. The vaccine of claim 1, wherein the pyridinyl group grafted polymer comprises a poly-4-vinylpyridine.

3. The vaccine of claim 1, wherein the pyridinyl group grafted polymer comprises a copolymer formed with 4-vinylpyridine monomers.

4. The vaccine of claim 3, wherein the copolymer is a random copolymer or a block copolymer.

5. The vaccine of claim 1, wherein the pyridinyl group grafted polymer comprises a poly-2-vinylpyridine.

6. The vaccine of claim 1, wherein the pyridinyl group grafted polymer comprises a copolymer formed with 2-vinylpyridine.

7. The vaccine of claim 6, wherein the copolymer is a random copolymer or a block copolymer.

8. The vaccine of claim 1, wherein the pyridinyl group grafted polymer comprises a pyridine grafted poly(ε-caprolactone) (PCL-py).

9. The vaccine of claim 1, wherein the pyridinyl group grafted polymer comprises a pyridine grafted poly(2-hydroxyethyl)methacrylate (pHEMA-py).

10. The vaccine of claim 1, wherein the pyridinyl group grafted polymer comprises grafting groups.

11. The vaccine of claim 10, wherein the grafting groups include a heterocycle group.

12. The vaccine of claim 11, wherein the heterocycle group comprises nitrogen atoms.

13. The vaccine of claim 11, wherein the heterocycle group comprises sulfur atoms.

14. A composition comprising the vaccine of claim 1.

15. The composition of claim 14, wherein the plurality of polymer-protein core-shell nanoparticles constitute about 0.001% to about 35% of the composition by weight.

* * * * *